(12) United States Patent
Cacka et al.

(10) Patent No.: US 6,920,659 B2
(45) Date of Patent: Jul. 26, 2005

(54) TOOTHBRUSH

(75) Inventors: Joe W. Cacka, Berthoud, CO (US); Howell H. Chiles, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

(21) Appl. No.: 10/045,953

(22) Filed: Jan. 12, 2002

(65) Prior Publication Data

US 2002/0120991 A1 Sep. 5, 2002

Related U.S. Application Data

(60) Provisional application No. 60/261,575, filed on Jan. 12, 2001.

(51) Int. Cl.[7] .............................................. A46B 13/00
(52) U.S. Cl. ....................................................... 15/22.1
(58) Field of Search ................................ 15/22.1, 22.2, 15/105

(56) References Cited

U.S. PATENT DOCUMENTS

| | | |
|---|---|---|
| 1,313,490 A | 8/1919 | Larson |
| 1,355,037 A | 10/1920 | Dziuk |
| 1,424,879 A | 8/1922 | Carlstedt |
| 1,517,320 A | 12/1924 | Stoddart |
| 1,696,835 A | 12/1928 | Burnett |
| 1,703,642 A | 2/1929 | Sticht |
| 1,796,641 A | 3/1931 | Zimmerman et al. |
| 1,832,519 A | 11/1931 | Wheat et al. |
| 1,880,617 A | 10/1932 | White |
| 2,016,597 A | 10/1935 | Drake |
| 2,044,863 A | 6/1936 | Sticht |
| 2,158,738 A | 5/1939 | Baker et al. |
| 2,206,726 A | 7/1940 | Lasater |
| 2,246,523 A | 6/1941 | Kulik |
| 2,278,365 A | 3/1942 | Daniels |
| 2,282,700 A | 5/1942 | Bobbroff |
| 2,598,275 A | 5/1952 | Lakin .............................. 74/36 |
| 2,705,335 A | 4/1955 | Glassman et al. |
| 2,709,227 A | 5/1955 | Foley et al. |
| 2,728,928 A | 1/1956 | Beeren ........................... 15/29 |
| 2,734,139 A | 2/1956 | Murphy |
| 2,806,235 A | 9/1957 | Carstairs et al. |
| 2,875,458 A | 3/1959 | Tsuda |
| 2,917,758 A | 12/1959 | Heid et al. |

(Continued)

FOREIGN PATENT DOCUMENTS

| | | |
|---|---|---|
| CH | 435553 | 10/1967 |
| CH | 609238 | 2/1979 |
| DE | 243224 | 4/1910 |

(Continued)

OTHER PUBLICATIONS

Sonex International: Brushing with the Ultima– The World's Only Dual–Frequency Ultrasonic Toothbrush, Jul. 28, 1999, published at Sonipic.com.

Teledyne Water Pik "Plaque Control 3000" plaque removal instrument (Jul. 1991).

American Dentronics Incorporated "Soniplak" sonic plaque removal system (May 1993).

(Continued)

*Primary Examiner*—Terrance T. Till
(74) *Attorney, Agent, or Firm*—Dorsey & Whitney LLP

(57) ABSTRACT

A power toothbrush including a handle and a brush head with bristles. In one embodiment, the toothbrush includes vibratory means for causing the brush head and the bristles to vibrate, and vibration isolation means for reducing the transfer of vibrations from the vibratory means to the handle. The vibratory means can include an eccentric motor positioned in the brush head or the brush shaft of the toothbrush. Vibration dampening material can be included in the vibration isolation means to reduce the transfer of vibrations to the handle.

22 Claims, 12 Drawing Sheets

U.S. PATENT DOCUMENTS

| | | | |
|---|---|---|---|
| 2,931,371 A | 4/1960 | Petitta | |
| 2,977,614 A | 4/1961 | Demanuele | |
| 3,104,405 A | 9/1963 | Perrinjaquet | |
| 3,106,216 A | 10/1963 | Kirby | |
| D197,048 S | 12/1963 | Troy | |
| D197,208 S | 12/1963 | Cassidy et al. | D9/2 |
| 3,143,697 A | 8/1964 | Springer | 320/2 |
| 3,145,404 A | 8/1964 | Fiedler | |
| D199,560 S | 11/1964 | Thompson | |
| D199,893 S | 12/1964 | Bond et al. | |
| 3,159,859 A | 12/1964 | Rasmussen | |
| 3,160,902 A | 12/1964 | Aymar | |
| 3,168,834 A | 2/1965 | Smithson | |
| 3,181,189 A | 5/1965 | Leyden | 15/22 |
| 3,183,538 A | 5/1965 | Hubner | |
| D202,873 S | 11/1965 | Husted | |
| D204,127 S | 3/1966 | Syvertson | |
| 3,270,416 A | 9/1966 | Massa | |
| 3,278,963 A | 10/1966 | Bond | |
| 3,316,576 A | 5/1967 | Urbrush | |
| 3,335,443 A | 8/1967 | Parisi et al. | |
| 3,346,748 A | 10/1967 | McNair | |
| 3,358,309 A | 12/1967 | Richardson | |
| D210,066 S | 2/1968 | Johnson | |
| 3,371,260 A | 2/1968 | Jackson et al. | 320/2 |
| D210,349 S | 3/1968 | Boldt | |
| 3,375,820 A | 4/1968 | Kuris et al. | |
| D212,208 S | 9/1968 | Rogers | D4/16 |
| 3,418,552 A | 12/1968 | Holmes | 320/2 |
| 3,421,524 A | 1/1969 | Waters | |
| 3,430,279 A | 3/1969 | Hintze | |
| 3,463,994 A | 8/1969 | Spohr | 320/2 |
| 3,466,689 A | 9/1969 | Aurello et al. | |
| 3,472,045 A | 10/1969 | Nelsen et al. | |
| 3,472,247 A | 10/1969 | Borsum et al. | |
| 3,474,799 A | 10/1969 | Cappello | |
| 3,535,726 A | 10/1970 | Sawyer | |
| 3,536,065 A | 10/1970 | Moret | |
| 3,538,359 A | 11/1970 | Barowski | |
| 3,552,022 A | 1/1971 | Axelsson | |
| 3,559,292 A | 2/1971 | Weissman | |
| 3,563,233 A | 2/1971 | Bodine | |
| 3,588,936 A | 6/1971 | Duve | |
| 3,590,814 A | 7/1971 | Bennett et al. | |
| D221,823 S | 9/1971 | Cook | D4/15 |
| 3,642,344 A | 2/1972 | Corker | |
| 3,651,576 A | 3/1972 | Massa | |
| 3,660,902 A | 5/1972 | Axelsson | |
| 3,667,483 A | 6/1972 | McCabe | |
| 3,672,378 A | 6/1972 | Silverman | |
| 3,676,218 A | 7/1972 | Sawyer | |
| 3,759,274 A | 9/1973 | Warner | |
| 3,760,799 A | 9/1973 | Crowson | |
| 3,809,977 A | 5/1974 | Balamuth et al. | |
| 3,831,611 A | 8/1974 | Hendricks | |
| 3,840,932 A | 10/1974 | Balamuth et al. | |
| 3,847,167 A | 11/1974 | Brien | |
| 3,882,364 A | 5/1975 | Wright et al. | |
| 3,902,510 A | 9/1975 | Roth | |
| 3,903,601 A | 9/1975 | Anderson et al. | |
| 3,967,617 A | 7/1976 | Krolik | |
| 3,978,852 A | 9/1976 | Annoni | |
| 3,980,906 A | 9/1976 | Kuris et al. | |
| 4,004,344 A | 1/1977 | Gold et al. | |
| 4,005,722 A | 2/1977 | Bragg | |
| 4,008,728 A | 2/1977 | Sanchez | |
| 4,014,354 A | 3/1977 | Garrett | |
| 4,019,522 A | 4/1977 | Elbreder | |
| 4,048,723 A | 9/1977 | Thorup | |
| 4,064,883 A | 12/1977 | Oldham | |
| 4,133,339 A | 1/1979 | Naslund | |
| 4,141,352 A | 2/1979 | Ebner et al. | |
| 4,177,434 A | 12/1979 | Ida | |
| D254,162 S | 2/1980 | Barker | D4/15 |
| 4,192,035 A | 3/1980 | Kuris | |
| 4,203,431 A | 5/1980 | Abura et al. | 128/39 |
| 4,205,664 A | 6/1980 | Baccialon | |
| 4,219,619 A | 8/1980 | Zarow | |
| 4,235,253 A | 11/1980 | Moore | |
| 4,245,658 A | 1/1981 | Lecouturier | |
| RE30,536 E | 3/1981 | Perdreaux, Jr. | |
| 4,255,693 A | 3/1981 | Keidl | |
| 4,265,257 A | 5/1981 | Salyer | |
| 4,271,382 A | 6/1981 | Maeda et al. | |
| 4,271,384 A | 6/1981 | Beiling et al. | |
| 4,271,854 A | 6/1981 | Bengtsson | |
| 4,275,363 A | 6/1981 | Mishiro et al. | |
| 4,289,486 A | 9/1981 | Sargeant | |
| 4,307,740 A | 12/1981 | Florindez et al. | |
| 4,319,377 A | 3/1982 | Tarrson et al. | |
| 4,319,595 A | 3/1982 | Ulrich | |
| 4,326,547 A | 4/1982 | Verplank | |
| 4,326,548 A | 4/1982 | Wagner | |
| 4,326,549 A | 4/1982 | Hinding | |
| 4,331,422 A | 5/1982 | Heyman | |
| 4,333,197 A | 6/1982 | Kuris | |
| D265,515 S | 7/1982 | Levin | |
| 4,338,957 A | 7/1982 | Meibauer | |
| 4,347,839 A | 9/1982 | Youngclaus, Jr. | |
| 4,353,141 A | 10/1982 | Teague, Jr. et al. | |
| 4,381,478 A | 4/1983 | Saijo et al. | |
| 4,395,665 A | 7/1983 | Buchas | |
| 4,397,327 A | 8/1983 | Hadary | |
| D272,565 S | 2/1984 | Levine | |
| D272,680 S | 2/1984 | Stocchi | D4/25 |
| 4,429,997 A | 2/1984 | Matthews | |
| 4,432,729 A | 2/1984 | Fattaleh | |
| 4,434,806 A | 3/1984 | Givens | |
| 4,442,830 A | 4/1984 | Markau | 128/66 |
| 4,458,702 A | 7/1984 | Grollimund | |
| 4,505,678 A | 3/1985 | Andersson | |
| 4,522,355 A | 6/1985 | Moran | |
| 4,522,595 A | 6/1985 | Selvidge | |
| 4,562,413 A | 12/1985 | Mishiro et al. | |
| 4,564,794 A | 1/1986 | Kilen et al. | |
| 4,576,190 A | 3/1986 | Youssef | |
| 4,577,649 A | 3/1986 | Shimenkov | |
| D283,374 S | 4/1986 | Cheuk-Yiu | D4/101 |
| 4,585,415 A | 4/1986 | Hommann | 433/80 |
| 4,586,521 A | 5/1986 | Urso | |
| 4,603,448 A | 8/1986 | Middleton et al. | |
| 4,605,025 A | 8/1986 | McSpadden | |
| 4,608,019 A | 8/1986 | Kumabe et al. | |
| 4,617,718 A | 10/1986 | Andersson | |
| 4,634,376 A | 1/1987 | Mossle et al. | |
| 4,644,937 A | 2/1987 | Hommann | 128/66 |
| 4,655,198 A | 4/1987 | Hommann | 128/66 |
| 4,698,869 A | 10/1987 | Mierau et al. | |
| 4,706,695 A | 11/1987 | Urso | |
| D294,885 S | 3/1988 | Mollenhoff | |
| 4,766,630 A | 8/1988 | Hegemann | 15/22 R |
| 4,787,847 A | 11/1988 | Martin et al. | |
| 4,791,940 A | 12/1988 | Hirshfeld et al. | |
| 4,811,445 A | 3/1989 | Lagieski et al. | |
| 4,820,153 A | 4/1989 | Romhild et al. | |
| 4,820,154 A | 4/1989 | Romhild et al. | |
| 4,827,550 A | 5/1989 | Graham et al. | 15/22 R |
| 4,832,063 A | 5/1989 | Smole | |
| D301,770 S | 6/1989 | Bethany | |
| 4,845,795 A | 7/1989 | Crawford et al. | 15/22 R |

| | | | | | |
|---|---|---|---|---|---|
| 4,856,133 A | 8/1989 | Sanchez ................... 15/29 | 5,261,430 A | 11/1993 | Mochel |
| D303,876 S | 10/1989 | Clemens et al. ............ D4/101 | 5,263,218 A | 11/1993 | Giuliani et al. |
| 4,871,396 A | 10/1989 | Tsujita et al. | D341,943 S | 12/1993 | Si-Hoe ................... D4/108 |
| 4,873,496 A | 10/1989 | Ohgihara et al. | 5,267,579 A | 12/1993 | Bushberger |
| 4,879,781 A | 11/1989 | Desimone | D343,064 S | 1/1994 | Reno |
| 4,880,382 A | 11/1989 | Moret et al. | 5,279,314 A | 1/1994 | Poulos et al. |
| 4,887,052 A | 12/1989 | Murakami et al. | 5,289,604 A | 3/1994 | Kressner |
| 4,913,133 A | 4/1990 | Tichy | 5,293,886 A | 3/1994 | Czapor |
| 4,913,176 A | 4/1990 | DeNiro | 5,294,896 A | 3/1994 | Kjellander et al. |
| 4,922,936 A | 5/1990 | Buzzi et al. | D346,212 S | 4/1994 | Hosl |
| D308,765 S | 6/1990 | Johnson | 5,305,492 A | 4/1994 | Giuliani et al. |
| 4,974,278 A | 12/1990 | Hommann ................. 15/22 R | 5,309,590 A | 5/1994 | Giuliani et al. |
| 4,989,287 A | 2/1991 | Scherer ..................... 15/22.1 | 5,309,591 A | 5/1994 | Hagele et al. ............. 15/22.1 |
| 4,991,249 A | 2/1991 | Suroff | 5,311,632 A | 5/1994 | Center |
| 4,995,403 A | 2/1991 | Beckman et al. | 5,311,633 A | 5/1994 | Herzog et al. ................ 15/28 |
| 5,000,684 A | 3/1991 | Odrich | 5,323,796 A | 6/1994 | Urso |
| 5,002,487 A | 3/1991 | Tichy | 5,337,435 A | 8/1994 | Krasner et al. .............. 15/23 |
| 5,007,127 A | 4/1991 | Paolo ...................... 15/29 | 5,341,534 A | 8/1994 | Serbinski et al. |
| 5,016,660 A | 5/1991 | Boggs | 5,353,460 A | 10/1994 | Bauman .................... 15/22.1 |
| 5,020,179 A | 6/1991 | Scherer ..................... 15/22.1 | 5,354,246 A | 10/1994 | Gotman ..................... 475/248 |
| 5,033,150 A | 7/1991 | Gross et al. | 5,355,638 A | 10/1994 | Hoffman .................... 451/32 |
| D318,918 S | 8/1991 | Hartwein | 5,358,328 A | 10/1994 | Inoue et al. .................. 366/65 |
| D319,363 S | 8/1991 | Uemura et al. ............ D6/534 | 5,359,747 A | 11/1994 | Amakasu .................... 15/22.1 |
| 5,050,625 A | 9/1991 | Siekmann | D353,490 S | 12/1994 | Hartwein ................... D4/108 |
| D321,285 S | 11/1991 | Hirabayashi | 5,369,831 A | 12/1994 | Bock |
| 5,062,797 A | 11/1991 | Gonser | D354,168 S | 1/1995 | Hartwein ................... D4/108 |
| 5,067,223 A | 11/1991 | Bruno | 5,378,153 A | 1/1995 | Giuliani et al. |
| D321,986 S | 12/1991 | Snyder et al. ............. D4/101 | 5,383,242 A | 1/1995 | Bigler et al. |
| 5,068,939 A | 12/1991 | Holland ..................... 15/22.1 | 5,393,229 A | 2/1995 | Ram |
| 5,069,621 A | 12/1991 | Paradis | 5,400,811 A | 3/1995 | Meibauer |
| 5,071,348 A | 12/1991 | Woog | 5,404,608 A | 4/1995 | Hommann |
| 5,072,477 A | 12/1991 | Pai | 5,406,664 A | 4/1995 | Hukuba |
| 5,072,482 A | 12/1991 | Bojar et al. ................ 15/180 | 5,406,965 A | 4/1995 | Levine |
| 6,068,939 A | 12/1991 | Holland | D358,486 S | 5/1995 | Loew .......................... D4/104 |
| 5,077,855 A | 1/1992 | Ambasz ..................... 15/22.1 | D358,713 S | 5/1995 | Perry |
| 5,085,236 A | 2/1992 | Odneal et al. | D358,801 S | 5/1995 | Vos ............................ D13/108 |
| 5,088,145 A | 2/1992 | Whitefield ................. 15/22.1 | 5,411,041 A | 5/1995 | Ritter |
| 5,094,256 A | 3/1992 | Barth | 5,412,827 A | 5/1995 | Muller et al. |
| 5,095,470 A | 3/1992 | Oka et al. | 5,416,942 A | 5/1995 | Baldacci et al. ............ 15/22.1 |
| 5,100,321 A | 3/1992 | Coss et al. | 5,419,346 A | 5/1995 | Tipp |
| 5,120,225 A | 6/1992 | Amit ......................... 433/216 | 5,419,703 A | 5/1995 | Warrin et al. |
| 5,123,841 A | 6/1992 | Millner | 5,421,726 A | 6/1995 | Okada |
| 5,125,837 A | 6/1992 | Warrin et al. | D363,605 S | 10/1995 | Kou et al. .................. D4/101 |
| 5,133,661 A | 7/1992 | Euvrard | 5,459,898 A | 10/1995 | Bacolot ..................... 15/106 |
| 5,138,733 A | 8/1992 | Bock | 5,467,494 A | 11/1995 | Muller et al. |
| 5,145,369 A | 9/1992 | Lustig et al. ............... 433/118 | 5,467,495 A | 11/1995 | Boland et al. ................ 15/28 |
| 5,150,492 A | 9/1992 | Suroff | 5,482,466 A | 1/1996 | Haynes |
| 5,151,030 A | 9/1992 | Comeaux | 5,484,281 A | 1/1996 | Renow et al. ................ 433/80 |
| 5,165,131 A | 11/1992 | Staar | 5,496,256 A | 3/1996 | Bock et al. |
| 5,169,313 A | 12/1992 | Kline | 5,499,420 A | 3/1996 | Boland ....................... 15/22.1 |
| 5,170,809 A | 12/1992 | Imai et al. | 5,504,958 A | 4/1996 | Herzog ...................... 15/22.1 |
| 5,174,314 A | 12/1992 | Charatan | 5,511,270 A | 4/1996 | Eliachar et al. |
| 5,176,157 A | 1/1993 | Mazza | 5,511,275 A | 4/1996 | Volpenhein et al. ....... 15/167.1 |
| 5,177,826 A | 1/1993 | Vrignaud et al. ........... 15/22.1 | D370,125 S | 5/1996 | Craft et al. |
| 5,180,363 A | 1/1993 | Idemoto et al. | D370,347 S | 6/1996 | Heinzelman et al. ....... D4/104 |
| 5,183,063 A | 2/1993 | Ringle et al. | 5,529,494 A | 6/1996 | Vlacancich ................ 433/105 |
| 5,184,632 A | 2/1993 | Gross et al. | D371,242 S | 7/1996 | Shimatsu et al. ........... D4/108 |
| 5,186,191 A | 2/1993 | Loubier | 5,545,968 A | 8/1996 | Hilfinger et al. |
| 5,188,133 A | 2/1993 | Romanus | 5,546,624 A | 8/1996 | Bock |
| 5,189,751 A | 3/1993 | Giuliani et al. | D375,841 S | 11/1996 | Serbinski ................... D4/108 |
| 5,198,732 A | 3/1993 | Morimoto | 5,573,020 A | 11/1996 | Robinson |
| 5,201,092 A | 4/1993 | Colson ....................... 15/167.1 | 5,577,285 A | 11/1996 | Drossler .................... 15/22.1 |
| 5,207,773 A | 5/1993 | Henderson | 5,579,786 A | 12/1996 | Wolk et al. |
| 5,213,434 A | 5/1993 | Hahn ......................... 403/59 | 5,588,452 A | 12/1996 | Peck |
| 5,214,819 A | 6/1993 | Kirchner .................... 15/22.1 | 5,606,984 A | 3/1997 | Gao |
| 5,217,031 A | 6/1993 | Santoro | 5,613,258 A | 3/1997 | Hilfinger et al. ............ 15/22.1 |
| 5,224,500 A | 7/1993 | Stella | 5,613,259 A | 3/1997 | Craft et al. |
| 5,226,206 A | 7/1993 | Davidovitz et al. | 5,617,601 A | 4/1997 | McDougall ................ 15/22.1 |
| 5,236,358 A | 8/1993 | Sieffert | 5,618,275 A | 4/1997 | Bock |
| 5,247,716 A | 9/1993 | Bock | 5,619,766 A | 4/1997 | Zhadanov et al. ........... 15/29 |
| 5,253,382 A | 10/1993 | Beny | 5,625,916 A | 5/1997 | McDougall ................. 15/28 |

| | | | | | | |
|---|---|---|---|---|---|---|
| 5,651,157 A | 7/1997 | Hahn | | 6,138,310 A | 10/2000 | Porper et al. |
| D382,407 S | 8/1997 | Craft et al. | | 6,140,723 A | 10/2000 | Matsui et al. |
| 5,652,990 A | 8/1997 | Driesen et al. ............... 15/28 | | 6,148,462 A | 11/2000 | Zseng |
| 5,678,274 A | 10/1997 | Liu ........................ 15/167.1 | | 6,154,912 A | 12/2000 | Li |
| 5,678,578 A | 10/1997 | Kossak et al. | | 6,165,131 A | 12/2000 | Cuse et al. |
| 5,697,117 A | 12/1997 | Craft | | 6,178,579 B1 | 1/2001 | Blaustein et al. |
| 5,700,146 A | 12/1997 | Kucar | | 6,183,254 B1 | 2/2001 | Cohen ........................ 433/92 |
| RE35,712 E | 1/1998 | Murayama | | 6,195,828 B1 | 3/2001 | Fritsch |
| 5,709,233 A | 1/1998 | Boland et al. | | 6,202,242 B1 | 3/2001 | Salmon et al. |
| 5,718,667 A | 2/1998 | Sugimoto et al. | | 6,203,320 B1 | 3/2001 | Williams et al. |
| 5,732,433 A | 3/1998 | Göcking et al. ............... 15/28 | | 6,230,354 B1 | 5/2001 | Sproat |
| 5,738,575 A | 4/1998 | Bock | | 6,230,717 B1 | 5/2001 | Marx et al. |
| 5,742,972 A | 4/1998 | Bredall et al. ............. 15/167.1 | | 6,237,178 B1 | 5/2001 | Krammer et al. |
| 5,749,380 A | 5/1998 | Zebuhr | | 6,253,404 B1 | 7/2001 | Boland et al. |
| 5,762,078 A | 6/1998 | Zebuhr | | 6,267,593 B1 | 7/2001 | Haczek et al. |
| 5,775,346 A | 7/1998 | Szyszkowski | | 6,299,444 B1 | 10/2001 | Cohen ........................ 433/91 |
| 5,784,742 A | 7/1998 | Giuliani et al. | | 6,308,358 B2 | 10/2001 | Gruber et al. |
| 5,784,743 A | 7/1998 | Shek ........................ 15/22.1 | | 6,308,359 B2 | 10/2001 | Fritsch et al. |
| 5,787,908 A | 8/1998 | Robinson | | 6,341,400 B1 | 1/2002 | Kobayashi et al. |
| 5,794,295 A | 8/1998 | Shen | | 6,343,396 B1 | 2/2002 | Simovitz et al. |
| 5,815,872 A | 10/1998 | Meginniss, III et al. ..... 15/22.1 | | 6,343,400 B1 | 2/2002 | Massholder et al. |
| 5,816,271 A | 10/1998 | Urso | | 6,347,425 B1 | 2/2002 | Fattori et al. |
| 5,827,064 A | 10/1998 | Bock | | 6,349,442 B1 | 2/2002 | Cohen et al. ................ 15/22.1 |
| D400,713 S | 11/1998 | Solanki ........................ D4/104 | | 6,353,956 B1 | 3/2002 | Berge |
| 5,836,030 A | 11/1998 | Hazeu et al. ................ 15/22.1 | | 6,360,395 B2 | 3/2002 | Blaustein et al. |
| 5,842,244 A | 12/1998 | Hilfinger et al. ............. 15/22.1 | | 6,363,565 B1 | 4/2002 | Paffrath |
| 5,850,655 A | 12/1998 | Göcking et al. ............... 15/28 | | 6,367,108 B1 | 4/2002 | Fritsch et al. |
| D403,511 S | 1/1999 | Serbinski ..................... D4/108 | | 6,374,448 B2 | 4/2002 | Seifert |
| 5,855,216 A | 1/1999 | Robinson | | 6,381,795 B1 | 5/2002 | Hofmann et al. |
| 5,862,558 A | 1/1999 | Hilfinger et al. ............... 15/28 | | 6,401,288 B1 | 6/2002 | Porper et al. |
| 5,864,911 A | 2/1999 | Arnoux et al. | | 6,421,865 B1 | 7/2002 | McDougall |
| 5,864,915 A | 2/1999 | Ra ............................ 15/167.1 | | 6,421,866 B1 | 7/2002 | McDougall |
| 5,867,856 A | 2/1999 | Herzog ........................ 15/22.4 | | 6,421,867 B1 | 7/2002 | Weihrauch |
| 5,893,175 A | 4/1999 | Cooper | | 6,422,867 B2 | 7/2002 | Lang et al. |
| 5,896,615 A | 4/1999 | Zaksenberg | | 6,434,773 B1 | 8/2002 | Kuo |
| 5,899,693 A | 5/1999 | Himeno et al. | | 6,446,294 B1 | 9/2002 | Specht |
| 5,901,397 A | 5/1999 | Hafele et al. | | 6,446,295 B1 | 9/2002 | Calabrese |
| D410,787 S | 6/1999 | Barre et al. | | 6,453,497 B1 | 9/2002 | Chiang et al. |
| 5,908,038 A | 6/1999 | Bennett ........................ 132/308 | | 6,453,498 B1 | 9/2002 | Wu |
| D411,769 S | 7/1999 | Wright | | 6,453,499 B1 | 9/2002 | Leuermann |
| 5,921,254 A | 7/1999 | Carlucci et al. | | 6,463,615 B1 | 10/2002 | Gruber et al. |
| 5,927,300 A | 7/1999 | Boland et al. | | 6,490,747 B1 | 12/2002 | Metwally |
| 5,927,976 A | 7/1999 | Wu | | 6,510,575 B2 | 1/2003 | Calabrese |
| 5,930,858 A | 8/1999 | Jung ........................ 15/22.1 | | 6,526,994 B1 | 3/2003 | Santoro |
| 5,931,170 A | 8/1999 | Wu | | 6,536,066 B2 | 3/2003 | Dickie |
| 5,934,908 A | 8/1999 | Woog et al. | | 6,564,940 B2 | 5/2003 | Blaustein et al. |
| 5,943,723 A | 8/1999 | Hilfinger et al. ............. 15/22.1 | | 6,574,820 B1 | 6/2003 | DePuydt et al. |
| 5,944,033 A | 8/1999 | Robinson | | 6,581,233 B1 | 6/2003 | Cheng |
| D414,937 S | 10/1999 | Cornu et al. ................. D4/104 | | 6,581,234 B2 | 6/2003 | Lee et al. |
| D414,939 S | 10/1999 | Pedro, Jr. et al. ............. D4/104 | | 6,588,042 B2 | 7/2003 | Fritsch et al. |
| 5,974,613 A | 11/1999 | Herzog ........................ 15/22.1 | | 6,599,048 B2 | 7/2003 | Kuo |
| 5,974,615 A | 11/1999 | Schwarz-Hartmann et al. ........................ 15/22.4 | | 6,622,333 B1 | 9/2003 | Rehkemper et al. |
| | | | | 6,647,577 B2 | 11/2003 | Tam |
| 5,987,681 A | 11/1999 | Hahn et al. | | D484,311 S | 12/2003 | Cacka et al. |
| 5,991,957 A | 11/1999 | Watanabe ................. 15/167.1 | | 6,654,979 B2 | 12/2003 | Calabrese |
| D417,960 S | 12/1999 | Moskovich et al. ......... D4/104 | | 6,665,901 B2 | 12/2003 | Driesen et al. |
| 6,000,083 A | 12/1999 | Blaustein et al. | | 6,691,363 B2 | 2/2004 | Huen |
| 6,009,589 A | 1/2000 | Driesen et al. ............. 15/167.1 | | 6,701,565 B2 | 3/2004 | Hafemann |
| 6,021,538 A | 2/2000 | Kressner et al. ............... 15/28 | | 6,721,986 B2 | 4/2004 | Zhuan |
| 6,026,828 A | 2/2000 | Altshuler | | 6,725,490 B2 | 4/2004 | Blaustein et al. |
| 6,032,313 A | 3/2000 | Tsang ........................ 15/22.1 | | 6,735,803 B2 | 5/2004 | Kuo |
| 6,035,476 A | 3/2000 | Underwood et al. | | 6,735,804 B2 | 5/2004 | Carlucci et al. |
| 6,047,711 A | 4/2000 | Wagner | | 6,739,012 B2 | 5/2004 | Grez et al. |
| 6,050,818 A | 4/2000 | Boland et al. | | 6,751,823 B2 | 6/2004 | Biro et al. |
| RE36,699 E | 5/2000 | Murayama | | 6,760,945 B2 | 7/2004 | Ferber et al. |
| D423,784 S | 5/2000 | Joulin | | 6,760,946 B2 | 7/2004 | DePuydt |
| 6,065,176 A | 5/2000 | Watanabe et al. .......... 15/167.1 | | 6,766,548 B1 | 7/2004 | Lukas et al. |
| 6,092,252 A | 7/2000 | Fischer et al. | | 6,766,549 B2 | 7/2004 | Klupt |
| 6,095,811 A | 8/2000 | Stearns | | 6,779,126 B1 | 8/2004 | Lin et al. |
| 6,102,700 A | 8/2000 | Haczek et al. | | 6,779,215 B2 | 8/2004 | Hartman et al. |
| 6,106,294 A | 8/2000 | Daniel | | 6,785,926 B2 | 9/2004 | Green |

| | | | | | | |
|---|---|---|---|---|---|---|
| 6,792,640 B2 | 9/2004 | Lev | | 2003/0182746 A1 | 10/2003 | Fattori et al. |
| 6,795,993 B2 | 9/2004 | Lin | | 2003/0192139 A1 | 10/2003 | Fattori et al. |
| 6,798,169 B2 | 9/2004 | Stratmann et al. | | 2003/0196283 A1 | 10/2003 | Eliav et al. |
| 6,799,346 B2 | 10/2004 | Jeng et al. | | 2003/0196677 A1 | 10/2003 | Wiseman |
| 6,802,097 B2 | 10/2004 | Häfliger et al. | | 2003/0204925 A1 | 11/2003 | Hall et al. |
| 6,813,793 B2 | 11/2004 | Eliav | | 2003/0213075 A1 | 11/2003 | Hui et al. |
| 6,813,794 B2 | 11/2004 | Weng | | 2003/0213076 A1 | 11/2003 | Schutz et al. |
| 2001/0016963 A1 | 8/2001 | Driesen et al. | | 2003/0221267 A1 | 12/2003 | Chan |
| 2001/0039955 A1 | 11/2001 | Winters et al. | | 2003/0221269 A1 | 12/2003 | Zhuan |
| 2002/0017474 A1 | 2/2002 | Blaustein et al. | | 2003/0226223 A1 | 12/2003 | Chan |
| 2002/0029988 A1 | 3/2002 | Blaustein et al. | | 2004/0010869 A1 | 1/2004 | Fattori et al. |
| 2002/0032941 A1 | 3/2002 | Blaustein et al. | | 2004/0010870 A1 | 1/2004 | McNair |
| 2002/0039720 A1 | 4/2002 | Marx et al. | | 2004/0010871 A1 | 1/2004 | Nishinaka et al. |
| 2002/0059685 A1 | 5/2002 | Paffrath | | 2004/0010872 A1 | 1/2004 | Chiang |
| 2002/0066147 A1 | 6/2002 | Schutz | | 2004/0016067 A1 | 1/2004 | Kraemer |
| 2002/0078514 A1 | 6/2002 | Blaustein et al. | | 2004/0016068 A1 | 1/2004 | Lee |
| 2002/0078974 A1 | 6/2002 | Kossak et al. | | 2004/0016069 A1 | 1/2004 | Lee |
| 2002/0084707 A1 | 7/2002 | Tang | | 2004/0019987 A1 | 2/2004 | Chu |
| 2002/0088068 A1 | 7/2002 | Levy et al. | | 2004/0025274 A1 | 2/2004 | Moskovich et al. |
| 2002/0095734 A1 | 7/2002 | Wong | | 2004/0034951 A1 | 2/2004 | Davies et al. |
| 2002/0100134 A1 | 8/2002 | Dunn et al. | | 2004/0045106 A1 | 3/2004 | Lam |
| 2002/0106607 A1 | 8/2002 | Horowitz | | 2004/0045107 A1 | 3/2004 | Egeresi |
| 2002/0108193 A1 | 8/2002 | Gruber | | 2004/0049867 A1 | 3/2004 | Hui |
| 2002/0116775 A1 | 8/2002 | Wong | | 2004/0049868 A1 | 3/2004 | Ng |
| 2002/0120991 A1 | 9/2002 | Cacka et al. | | 2004/0060132 A1 | 4/2004 | Gatzemayer et al. |
| 2002/0121283 A1 | 9/2002 | Piccolo et al. | | 2004/0060134 A1 | 4/2004 | Eliav et al. |
| 2002/0129454 A1 | 9/2002 | Hilscher et al. | | 2004/0060135 A1 | 4/2004 | Gatzemayer et al. |
| 2002/0138926 A1 | 10/2002 | Brown, Jr. et al. | | 2004/0060136 A1 | 4/2004 | Gatzemayer et al. |
| 2002/0152563 A1 | 10/2002 | Sato | | 2004/0060137 A1 | 4/2004 | Eliav |
| 2002/0152564 A1 | 10/2002 | Blaustein et al. | | 2004/0068811 A1 | 4/2004 | Fulop et al. |
| 2002/0162180 A1 | 11/2002 | Blaustein et al. | | 2004/0074026 A1 | 4/2004 | Blaustein et al. |
| 2002/0166188 A1 | 11/2002 | Driesen et al. | | 2004/0083566 A1 | 5/2004 | Blaustein et al. |
| 2002/0170570 A1 | 11/2002 | Bergman | | 2004/0087882 A1 | 5/2004 | Roberts et al. |
| 2002/0174498 A1 | 11/2002 | Li | | 2004/0088806 A1 | 5/2004 | DePuydt et al. |
| 2002/0178519 A1 | 12/2002 | Zarlengo | | 2004/0088807 A1 | 5/2004 | Blaustein et al. |
| 2002/0184719 A1 | 12/2002 | Eliav et al. | | 2004/0091834 A1 | 5/2004 | Rizoiu et al. |
| 2002/0185149 A1 | 12/2002 | Ali | | 2004/0107521 A1 | 6/2004 | Chan et al. |
| 2003/0005544 A1 | 1/2003 | Felix | | 2004/0123409 A1 | 7/2004 | Dickie |
| 2003/0029472 A1 | 2/2003 | Adler | | 2004/0128777 A1 | 7/2004 | Koh |
| 2003/0031979 A1 | 2/2003 | Shortt et al. | | 2004/0128778 A1 | 7/2004 | Wong |
| 2003/0033679 A1 | 2/2003 | Fattori et al. | | 2004/0128779 A1 | 7/2004 | Chan et al. |
| 2003/0033680 A1 | 2/2003 | Davies et al. | | 2004/0128780 A1 | 7/2004 | Chan |
| 2003/0041396 A1 | 3/2003 | Dickie | | 2004/0134001 A1 | 7/2004 | Chan |
| 2003/0041397 A1 | 3/2003 | Hafemann | | 2004/0143917 A1 | 7/2004 | Ek |
| 2003/0066145 A1 | 4/2003 | Prineppi | | 2004/0154112 A1 | 8/2004 | Braun et al. |
| 2003/0074751 A1 | 4/2003 | Wu | | 2004/0154113 A1 | 8/2004 | Drossier et al. |
| 2003/0079305 A1 | 5/2003 | Takahata et al. | | 2004/0158944 A1 | 8/2004 | Fattori |
| 2003/0084525 A1 | 5/2003 | Blaustein et al. | | 2004/0163191 A1 | 8/2004 | Cuffaro et al. |
| 2003/0084526 A1 | 5/2003 | Brown et al. | | 2004/0168269 A1 | 9/2004 | Kunita et al. |
| 2003/0084527 A1 | 5/2003 | Brown et al. | | 2004/0168270 A1 | 9/2004 | Choi et al. |
| 2003/0084528 A1 | 5/2003 | Chan et al. | | 2004/0168271 A1 | 9/2004 | McDougall |
| 2003/0097723 A1 | 5/2003 | Li | | 2004/0168272 A1 | 9/2004 | Prineppi |
| 2003/0098037 A1 | 5/2003 | Dougan et al. | | 2004/0177458 A1 | 9/2004 | Chan et al. |
| 2003/0101526 A1 | 6/2003 | Hilscher et al. | | 2004/0187889 A1 | 9/2004 | Kemp et al. |
| 2003/0106175 A1 | 6/2003 | Lam | | 2004/0200016 A1 | 10/2004 | Chan et al. |
| 2003/0106565 A1 | 6/2003 | Andrews | | | | |
| 2003/0111091 A1 | 6/2003 | Hotta et al. | | FOREIGN PATENT DOCUMENTS | | |
| 2003/0126699 A1 | 7/2003 | Blaustein et al. | | | | |
| 2003/0131427 A1 | 7/2003 | Hilscher et al. | | DE | 17 66 651 C2 | 12/1981 |
| 2003/0140435 A1 | 7/2003 | Eliav et al. | | DE | 3431481 | 2/1986 |
| 2003/0140436 A1 | 7/2003 | Gatzemeyer et al. | | DE | 35 12 190 A1 | 10/1986 |
| 2003/0140437 A1 | 7/2003 | Eliav et al. | | DE | 8626725 | 5/1987 |
| 2003/0140937 A1 | 7/2003 | Cook | | DE | 37 36 308 A1 | 7/1989 |
| 2003/0140939 A1 | 7/2003 | Nudo, Sr. | | DE | 41 42 404 C2 | 7/1991 |
| 2003/0150474 A1 | 8/2003 | Doyscher | | DE | 40 03 305 A1 | 8/1991 |
| 2003/0154568 A1 | 8/2003 | Boland et al. | | DE | 42 23 195 A1 | 1/1994 |
| 2003/0162146 A1 | 8/2003 | Shortt et al. | | DE | 42 23 196 A1 | 1/1994 |
| 2003/0163881 A1 | 9/2003 | Driesen et al. | | DE | 42 26 659 A1 | 2/1994 |
| 2003/0163882 A1 | 9/2003 | Blaustein et al. | | DE | 43 09 078 A1 | 9/1994 |
| 2003/0182743 A1 | 10/2003 | Gatzemeyer et al. | | DE | 297 15 234 U1 | 12/1997 |
| 2003/0182744 A1 | 10/2003 | Fattori et al. | | DE | 29919053 | 1/2001 |

| | | |
|---|---|---|
| EP | 0 354 352 | 2/1990 |
| EP | 0 661 025 B1 | 7/1995 |
| FR | 429447 | 9/1911 |
| FR | 1171337 | 1/1959 |
| FR | 899618 | 6/1962 |
| GB | 477799 | 1/1938 |
| GB | 500517 | 2/1939 |
| GB | 1582558 | 8/1977 |
| GB | 2175494 | 12/1986 |
| JP | 33753 | 3/1978 |
| JP | 3-222905 A | 10/1991 |
| SE | 324221 | 5/1970 |
| WO | WO 91/13570 | 9/1991 |
| WO | WO 91/19437 | 12/1991 |
| WO | WO 92/10146 | 10/1992 |
| WO | WO 92/16160 | 10/1992 |
| WO | WO 93/10721 | 6/1993 |
| WO | WO 93/15628 | 8/1993 |
| WO | WO 94/04093 | 3/1994 |
| WO | WO 94/26144 | 11/1994 |
| WO | WO 95/02375 | 1/1995 |
| WO | WO 95/33419 | 12/1995 |
| WO | WO 01/28452 A1 | 4/2001 |
| WO | WO 01/28452 | 4/2001 |
| WO | WO 01/45582 A1 | 6/2001 |

OTHER PUBLICATIONS

Design of a Toothbrush, p. 361, Danish Official Design Gazette, published May 16, 1997.

Teledyne Water Pik "Sensonic" Toothbrush, sales brochure (at least as early as Sep. 1994).

Design of a Toothbrush, page 361, Danish Official Design Gazette, published May 16, 1997.

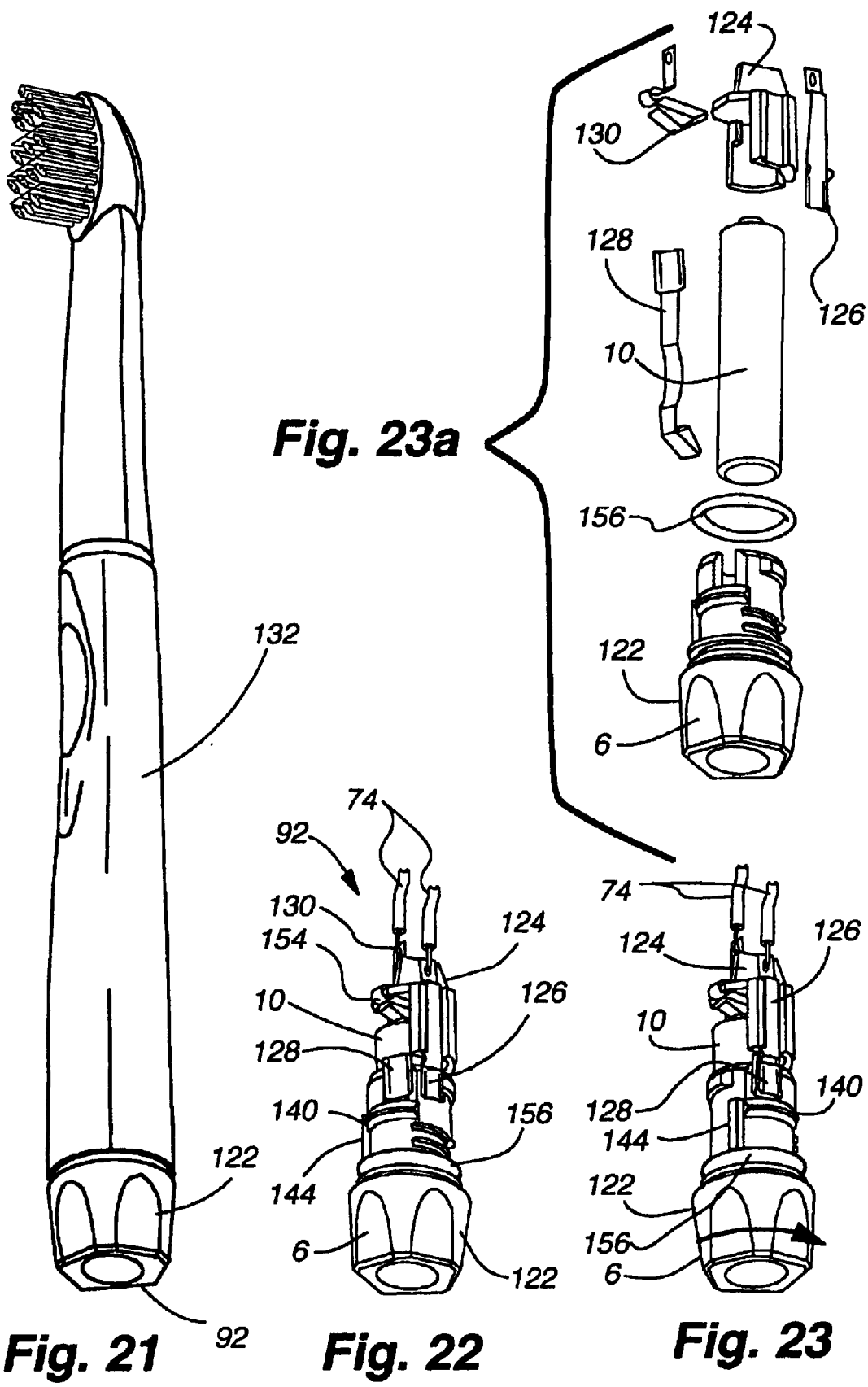

TOOTHBRUSH

CROSS-REFERENCE TO RELATED APPLICATION

This application claims priority, under 35 U.S.C. 119, of U.S. provisional patent application Ser. No. 60/261,515 entitled "Toothbrush with Motor Integrated with Vibrating Head," filed Jan. 12, 2001, the disclosure of which is hereby incorporated by reference in its entirety.

FIELD OF THE INVENTION

This invention relates to a powered toothbrush, and more specifically relates to a powered toothbrush having a vibrating toothbrush head isolated from the main handle.

BACKGROUND OF THE INVENTION

Typically, electric toothbrushes include a motor in the handle which drives a motion-creating mechanism, which in turn causes the toothbrush head to vibrate during use. The vibration of the head enhances the cleaning of one's teeth.

Often times, however, the vibration caused by the motor not only vibrates the brush head, but also vibrates the handle. Some users are annoyed by large vibrations of the handle. In addition, excessive vibration of the handle is an indication of an inefficient drive system which expends energy to drive not only the brush head but also the handle.

It is with these shortcomings in mind that embodiments of the invention have been developed.

SUMMARY OF THE INVENTION

According to one aspect of one embodiment of the invention, disclosed herein is a toothbrush which includes a handle, a brush shaft, a brush head with bristles, vibratory means for causing the brush head and the bristles to vibrate, and vibration isolation means for reducing the transfer of vibrations from the vibratory means to the handle.

In accordance with one embodiment of the present invention, a toothbrush includes a vibratory source (i.e., a motor) located in or near the brush head, and in order to reduce vibrations in the handle of a toothbrush, the portion of the toothbrush which contains the vibratory source is vibrationally isolated from the rest of the structure of the toothbrush.

In one embodiment, the brush head and brush shaft are vibrationally isolated from the handle by positioning the vibration isolation means between the vibratory means and the handle. In this embodiment, the vibratory means can be located anywhere along the brush shaft, or in the brush head.

In another embodiment, the vibratory source is located inside the brush head such that the vibratory source and brush head are vibrationally isolated from the brush shaft and the handle. Alternatively, the vibratory source is located inside the brush head such that the vibratory source and brush head are vibrationally isolated from the brush shaft and handle by locating an isolation structure at the brush shaft/handle intersection.

In addition, the brush shaft, which generally extends between the handle and the brush head, could be a flexible member which forms the vibration isolation structure between the brush head and motor from the shaft.

In one embodiment, the motor is driven by electricity supplied from a battery positioned in the handle. The battery can be replaceable or rechargeable. Wires may run from the battery through the handle, through an on/off switch, through the brush shaft, and to the location where the motor is located in order to supply the motor with electricity.

The features, utilities and advantages of the various embodiments of the invention will be apparent from the following more particular description of embodiments of the invention as illustrated in the accompanying drawings.

BRIEF DESCRIPTION OF THE DRAWINGS

FIG. 21 is a front perspective view of a toothbrush, in accordance with one embodiment of the present invention.

FIG. 22 is a side view of the end cap of a toothbrush, in accordance with one embodiment of the present invention.

FIG. 23 is a front perspective view of the end cap of FIG. 22, in accordance with one embodiment of the present invention.

DETAILED DESCRIPTION OF THE INVENTION

Disclosed herein, in one embodiment, is a toothbrush with vibratory means that cause the toothbrush head to vibrate, and a vibration isolation structure for isolating from the toothbrush handle the vibrations caused by the vibratory means.

Figure 3:
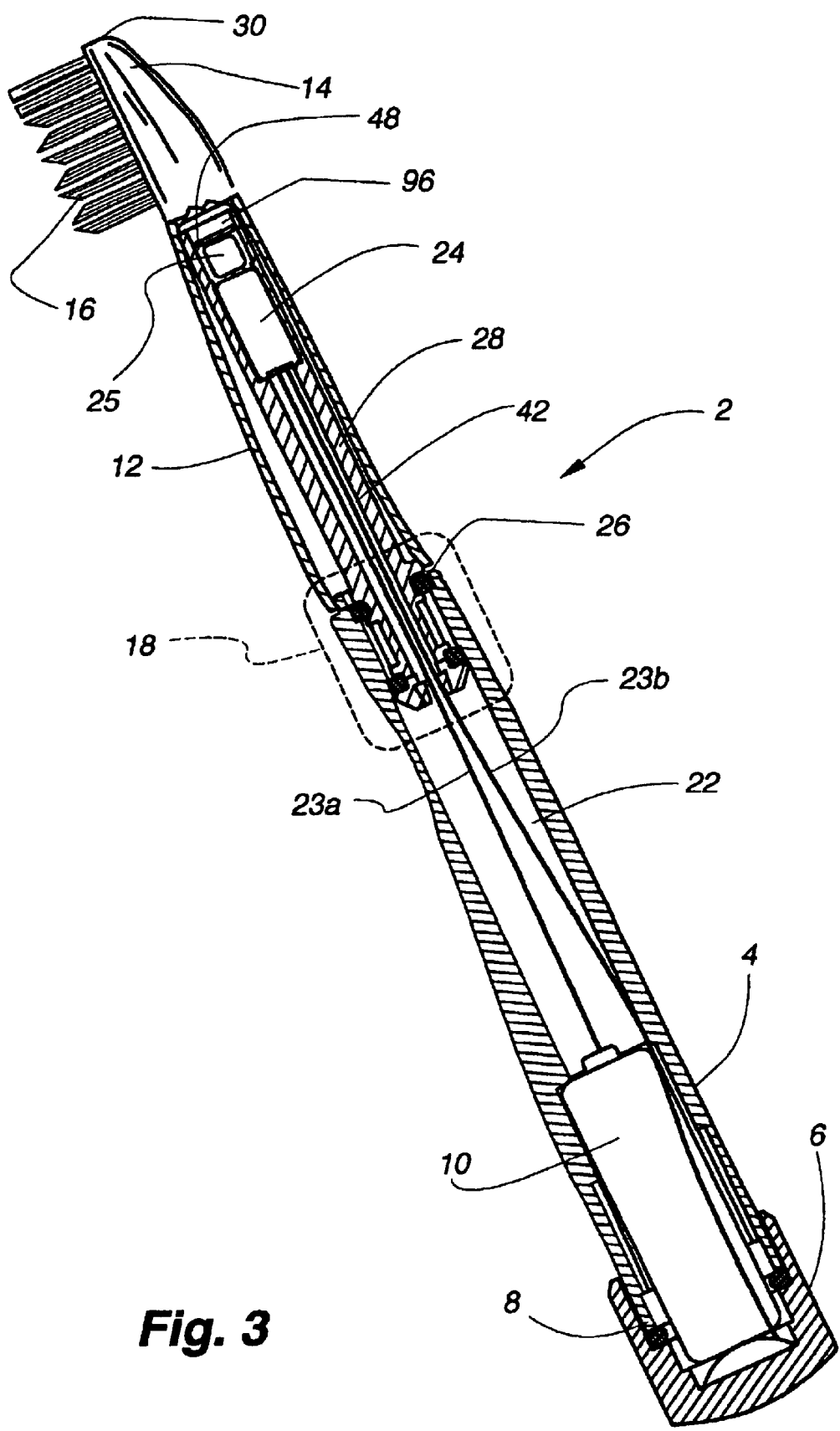
FIG. 3 is a side section view taken along line 3—3 of FIG. 2, in accordance with one embodiment of the present invention.

Generally and as shown in the example of FIG. 3, an isolation structure or joint 18 is located between the vibratory means (in one example, a motor 24 located within brush shaft 12) and the handle 4. The isolation structure 18 allows the portion of the toothbrush that includes the vibratory means to move in a vibrating manner independent of the handle or portions of the toothbrush on the side of the isolation structure opposite from the vibratory means. The purpose of isolation structure 18 is to reduce, modify, minimize, or attenuate the amount of vibration felt in handle 4 caused by the vibratory means 24 vibrating in brush shaft 12 (or elsewhere), while permitting the brush shaft 12 and the bristles 16 to move or vibrate.

Figures 1, 2:
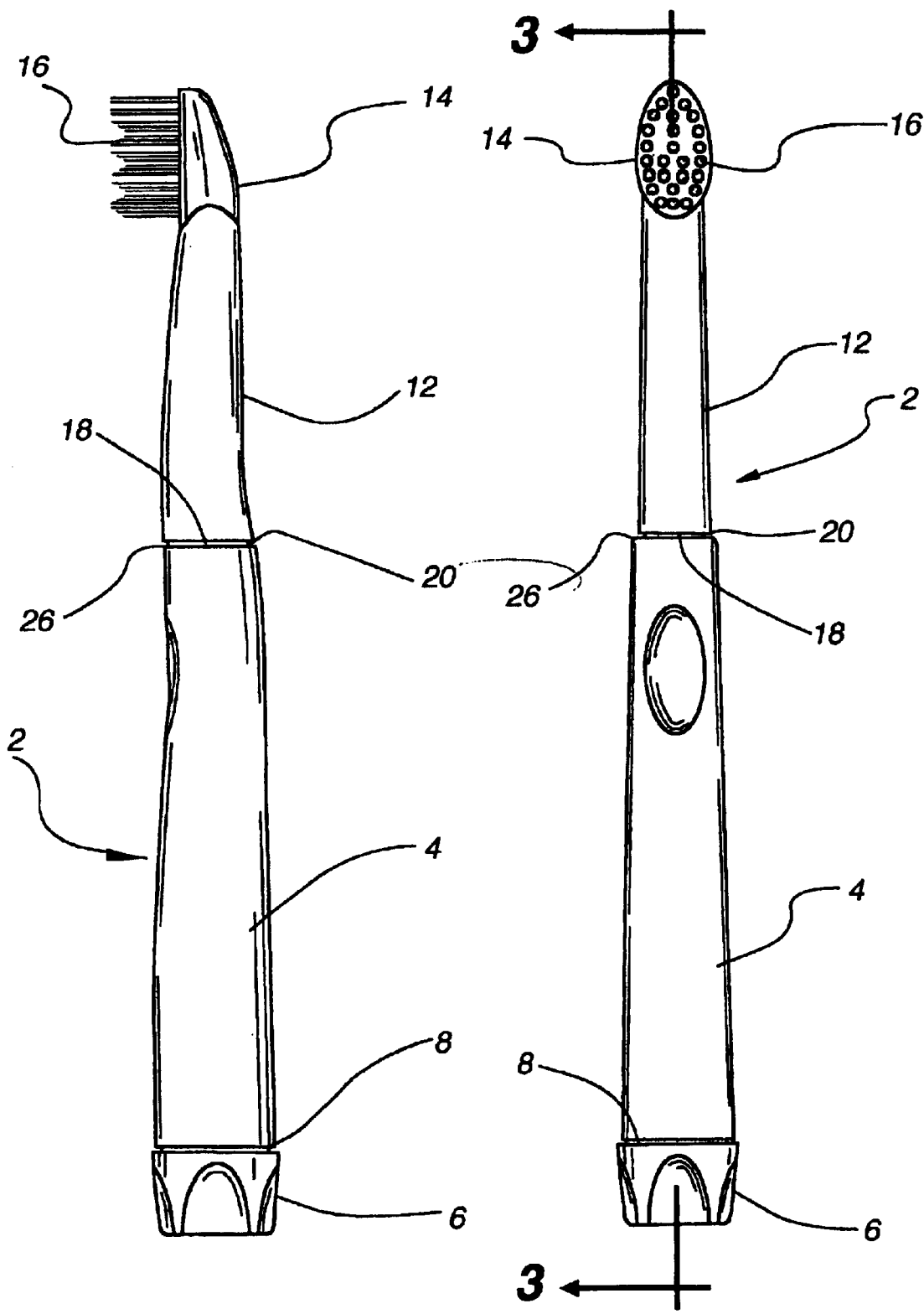
FIG. 1 is a side view of a toothbrush, in accordance with one embodiment of the present invention.
FIG. 2 is a front view of the embodiment illustrated in FIG. 1, in accordance with one embodiment of the present invention.

Referring now to FIGS. 1–2, the exterior of one embodiment of a toothbrush 2 is shown. Toothbrush 2 includes a handle 4, an end cap 6 attached to one end of the handle, and a brush shaft 12 attached to an end 8 of the handle opposite the end cap 6. A brush head 14 is attached to the end of the brush shaft 12, and bristles 16 extend outwardly from a surface of the brush head 14. Brush shaft 12 and brush head 14 may be integrally formed. The brush shaft 12 is attached to handle 4 about a motor shaft 28 (FIG. 3) connected at isolation structure 18, in one example. In the embodiment illustrated in FIGS. 1–2, a slight gap or annular spacing 20 is defined around the isolation structure 18 between the brush shaft 12 and handle 4 to allow brush shaft 12 to move with respect to handle 4 in a vibratory manner.

FIG. 3 is a representational cross-sectional view of one embodiment of toothbrush 2 and shows the internal mechanisms thereof. As illustrated in FIG. 3, a battery 10 is positioned inside handle 4. The battery supplies energy to vibratory means located in the brush head via wire leads 23a,b. The base or end cap 6 is attached to an end of the handle 4 to hold the battery inside the handle. End cap 6 can be taken off handle 4 to allow the battery 10 to be replaced. End cap 6 also may act as an on/off switch to control the actuation of the motor 24.

Figure 4:
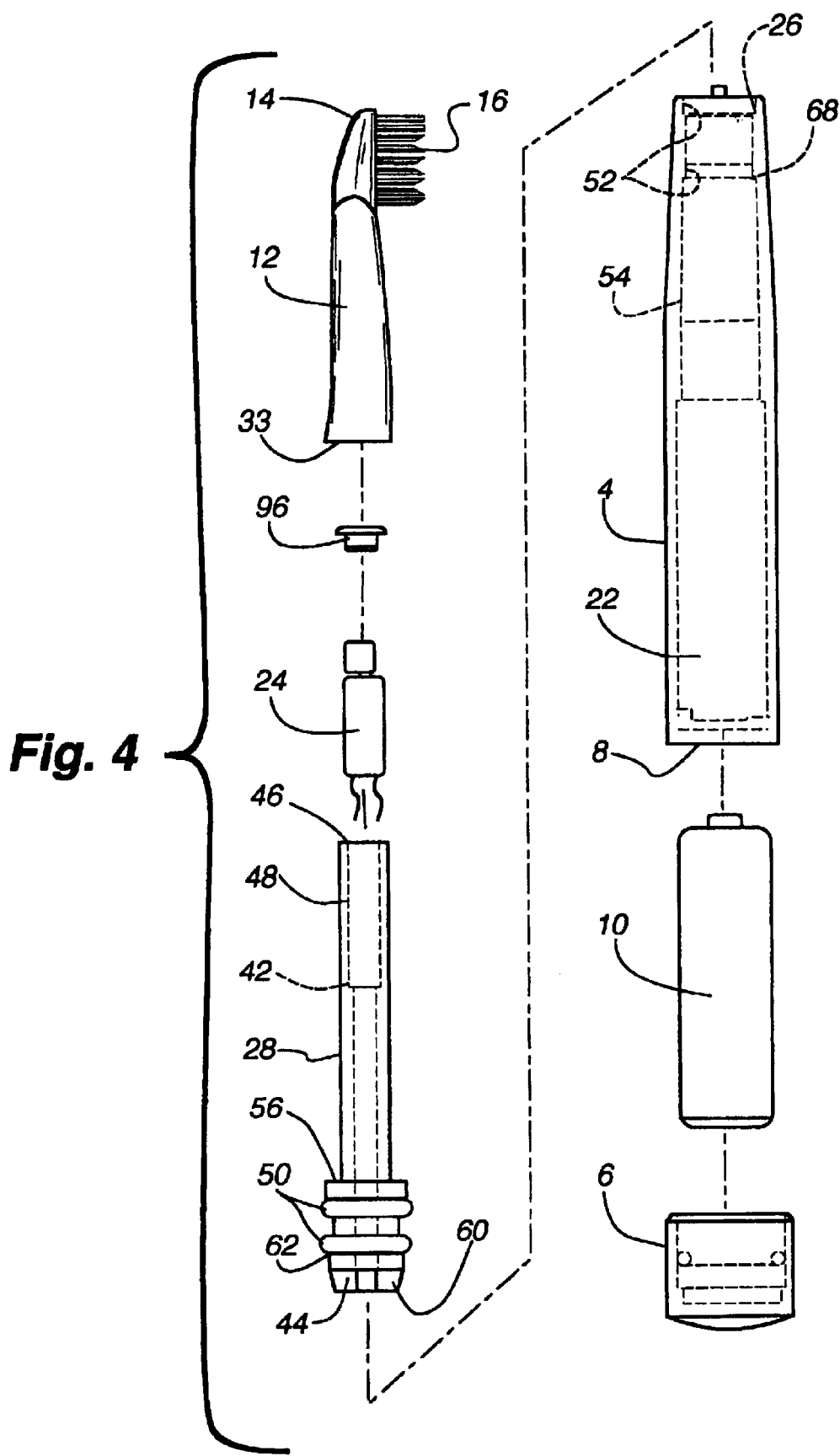
FIG. 4 is an exploded view of the embodiment illustrated in FIG. 1, in accordance with one embodiment of the present invention.

As shown in FIGS. 3–4, brush shaft 12 attaches to an opposite end 26 of handle 4 about motor shaft 28 positioned inside brush shaft 12. Bristle tufts 16 are attached to brush head 14 in a known manner.

Figure 5:
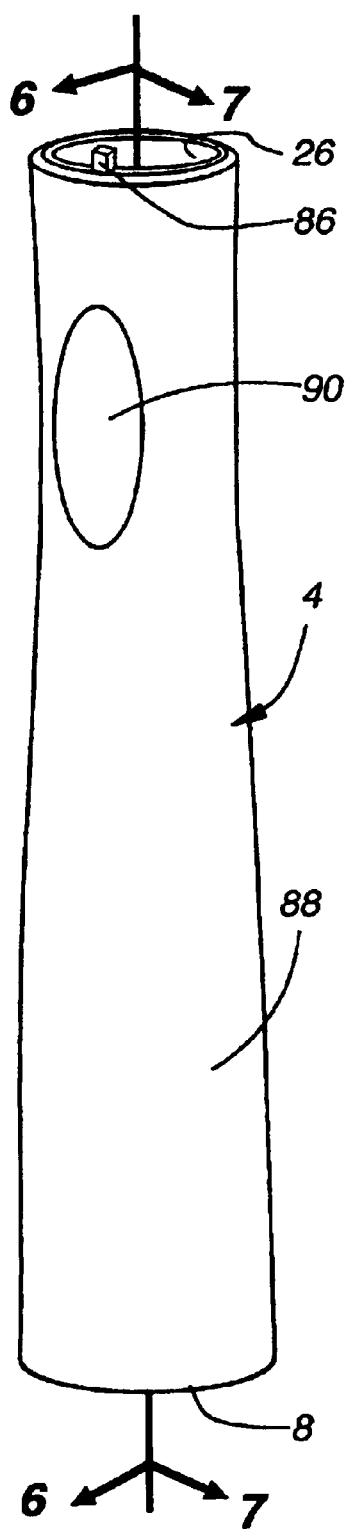
FIG. 5 is a front perspective view of the handle portion of a toothbrush, in accordance with one embodiment of the present invention.
Figure 6:
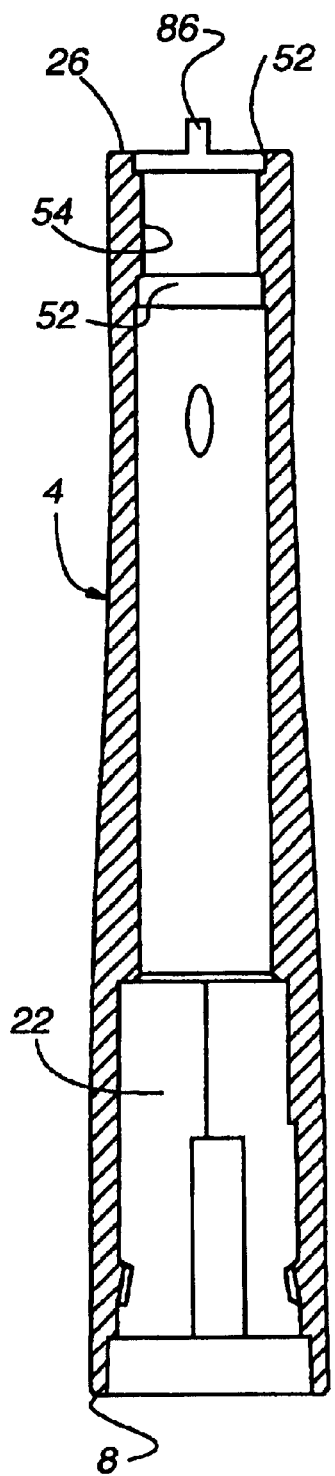
FIG. 6 is a front section view taken along line 6—6 of FIG. 13, in accordance with one embodiment of the present invention.
Figure 7:
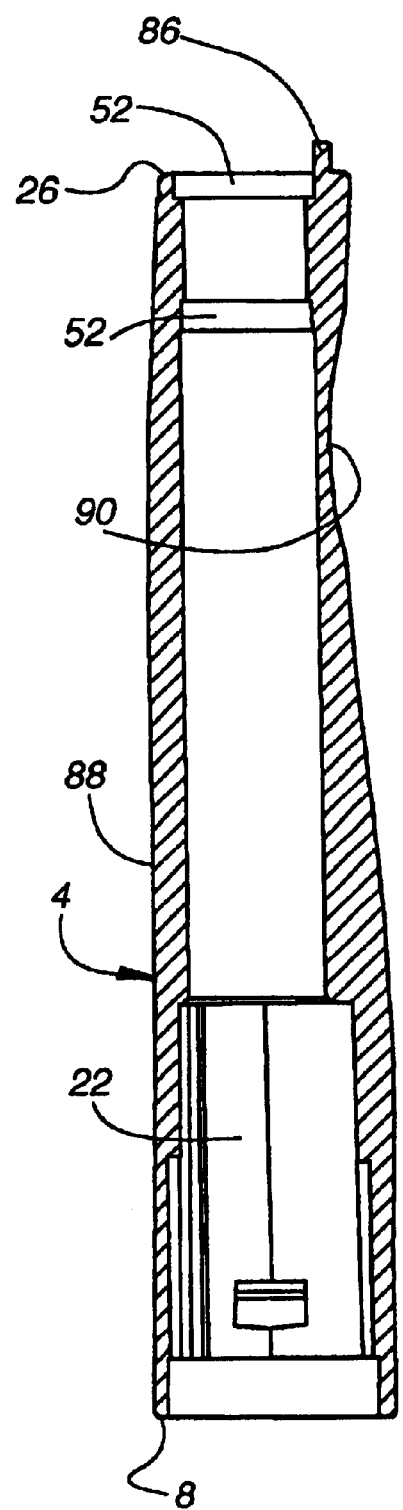
FIG. 7 is a side section view taken along line 7—7 of FIG. 13, in accordance with one embodiment of the present invention.
Figure 8:
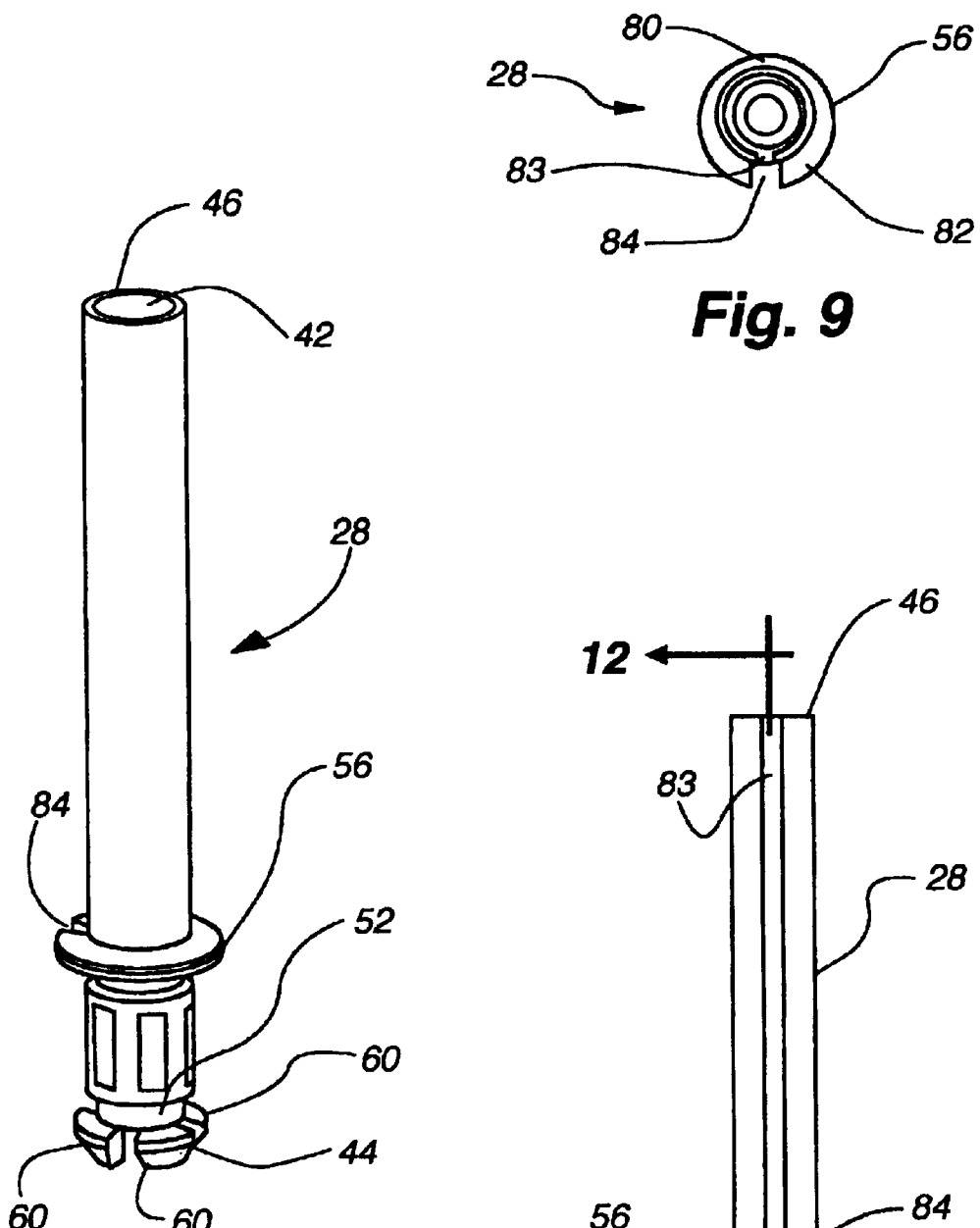
FIG. 8 is a front perspective view of the motor shaft of a toothbrush, in accordance with one embodiment of the present invention.
Figure 9:
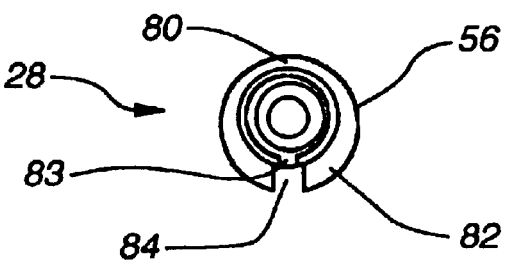
FIG. 9 is a top view of the motor shaft illustrated in FIG. 8, in accordance with one embodiment of the present invention.

FIGS. 5–7 show handle 4 according to one embodiment of the present invention. Generally, handle 4 is hollow and cylindrically shaped with a smaller diameter top end 26 and large diameter bottom end 8, in one example. Handle 4 defines an open lower end 8 which has a slightly larger diameter than an open upper end 26. As shown in FIGS. 6–7, axial recess 22 is formed within handle 4 from top end 26 to bottom end 8. Axial recess 22 is used to hold the battery 10 or other power source and acts as a conduit for the electrical wire leads which are connected between power source 10 and vibratory means 24 located elsewhere in the toothbrush.

In FIG. 6, adjacent the top end 26 of handle 4 on inside walls 54 of handle 4 are annular grooves 52 for receiving O-rings 50 (FIG. 4) positioned about a portion of motor shaft 28. As described further below, a protrusion 86 (FIGS. 5–7) extends from top open end 26 of handle 4 for ensuring that motor shaft 28, brush shaft 12 and handle 4 are properly oriented together.

Referring to FIGS. 4, 6–7, depending on the type of end cap 6 used, the interior walls of the handle 4 adjacent the bottom end 8 may include detents or threads for releasably securing the end cap to the bottom end of the handle. The front face of handle 4 may also include either an opening or a depressed area 90. The opening or depressed area may act as a recessed area adapted to a user's thumb, or may be configured as a control button for the device in another embodiment.

As illustrated in FIGS. 3–4, the brush shaft 12 is positioned about motor shaft 28 which is connected with open upper end 26 of handle 4. The brush shaft defines a housing which may be cylindrical and includes a closed upper end and open bottom end. The upper end of the motor shaft 28 is received within the open bottom end of the brush shaft. Vibratory means 24, such as a motor, are retained within the upper end of the motor shaft 28, in one example.

More specifically, open upper end 26 of handle 4 is attached to brush shaft 12 through motor shaft 28. Isolation structure 18 is formed at the region between open top end 26 of handle 4 and bottom end 44 of motor shaft 28.

In FIG. 3, brush shaft 12 forms a housing along most of its length up to brush head 14. Towards an end 30 of brush head 14, brush shaft 12 slims down to allow for convenient manipulation of brush head 14 in the user's mouth.

Figure 12:
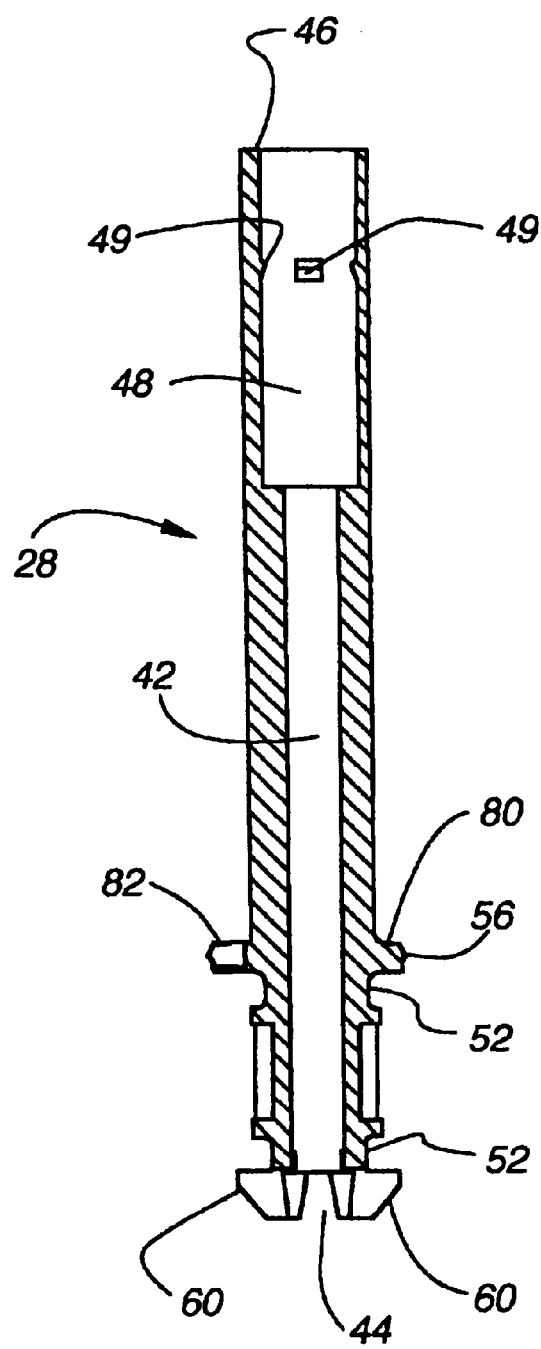
FIG. 12 is a side section view taken along line 12—12 in FIG. 10, in accordance with one embodiment of the present invention.

Motor shaft 28 is received within brush shaft 12. Motor shaft 28 is generally long and cylindrical in shape with a cylindrical cavity or bare 42 extending from one end 44 to the other 46 (FIG. 12). As shown in FIG. 4, one end 44 of motor shaft 28 is constructed to insert into open top end 26 of handle 4 to connect motor shaft 28 which forms isolation joint 18. The other end 46 of motor shaft 28 defines a motor receiving cavity 48 for secure placement of vibratory means 24.

FIGS. 8–12 show one example of motor shaft 28. Motor shaft 28 defines a top end 46 and a bottom end 44. Referring to FIG. 12, a bore 42 runs axially through top end 46 to bottom end 44. As shown in FIG. 3, the electrical wires 23a,b between the power supply 10 and motor 24 run through this axial bore 42. In FIG. 12, the bore also defines a cavity 48 for receiving vibratory means such as an eccentric motor. In at least one embodiment, the interior walls of the motor receiving cavity 48 include detents protrusions 49 for securing the motor within the cavity 48.

Bottom end 44 of motor shaft 28 is adapted to be attached to open top end 26 of handle 4. Bottom end 44 of motor shaft 28 defines axially extending fingers 60 that help engage bottom end 44 of motor shaft 28 with handle 4. As shown in FIG. 11, bottom end 44 of motor shaft 28 also defines O-ring grooves 52 for receiving O-rings 50. A flange 56 is defined annularly around motor shaft 28. In one embodiment, flange 56 is narrowest at the top 80 and widest at the bottom 82, where it defines a key slot 84 (FIGS. 8, 9, 10) for receiving the protrusion 86 extending off open top end 26 of handle 4. This ensures that motor shaft 28 and handle 4 are properly oriented together. Preferably, the protrusion 86 is received in the key slot 84 but does not physically contact the interior walls of key slot 84.

Figure 10:
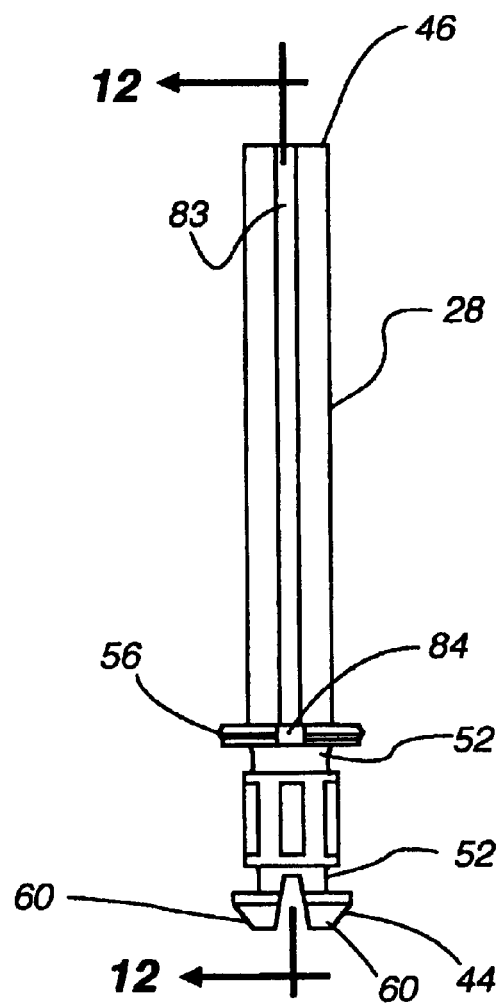
FIG. 10 is a front view of the motor shaft illustrated in FIG. 8, in accordance with one embodiment of the present invention.
Figure 11:
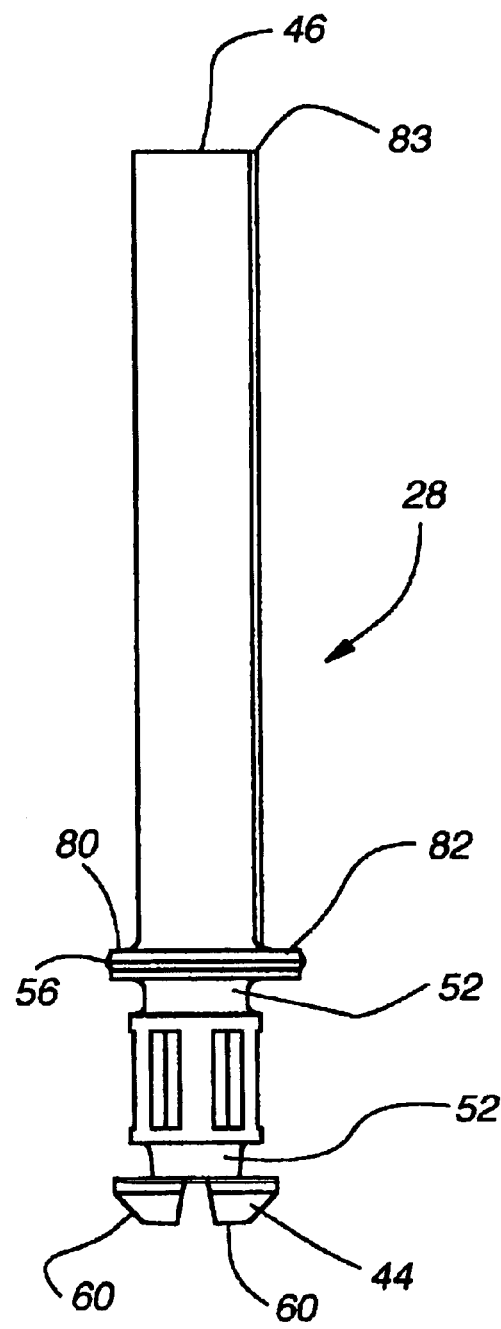
FIG. 11 is a side view of the motor shaft illustrated in FIG. 8, in accordance with one embodiment of the present invention.

As shown in FIG. 10, motor shaft 28 has a raised ridge 83, extending axially along the length of motor shaft 28. The interior wall of brush shaft 12 may have a notch, extending axially along a portion of the length of the brush shaft, to receive the raised ridge 83 of the motor shaft 28. The raised ridge and axial notch act to orient and guide brush shaft 12 into proper relative position as a user places brush shaft 12 about motor shaft 28.

Since brush shaft 12 covers motor shaft 28, and in combination is attached as described above to handle 4, by keying motor shaft 28 to handle 4 the proper orientation of toothbrush 2 with respect to handle 4 is obtained. Protrusion 86 on handle 4 extends axially from side 88 of handle 4 where a thumb depression/on-off button 90 may be formed.

As mentioned above, a flange 56 is formed on motor shaft 28 above the innermost O-ring 50. Flange 56 is contacted by bottom 33 of brush shaft 12 (see FIG. 4). Flange 56 helps keep brush shaft 12 from being pushed too far out over motor shaft 28, and also helps keep motor shaft 28 from being pushed too far into handle housing 4.

Figure 13:
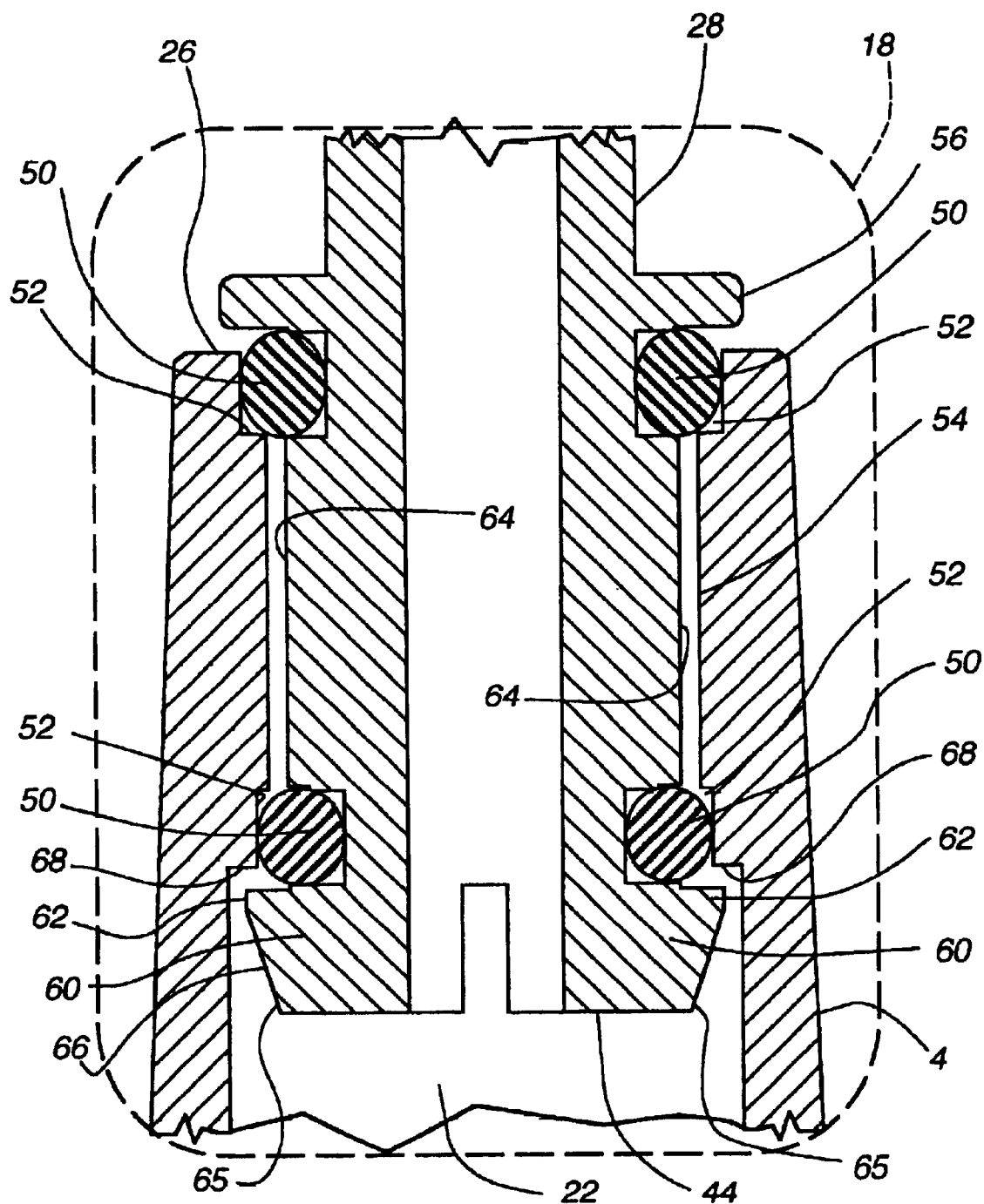
FIG. 13 is an enlarged section view of the isolation structure in the embodiment illustrated in FIG. 3.

Referring to FIG. 13, motor shaft 28 is retained within the handle 4 by a snap fit structure, which in one embodiment acts as an isolation joint 18. The first end 44 of motor shaft 28 defines flexible separated fingers 60 extending axially from the first end 44 of motor shaft 28. Each finger 60 defines an outwardly extending overhang 62 that extends radially outwardly from outer surface 64 of motor shaft 28 as defined between the pair of O-rings 50. Overhang 62 creates a sloped surface 65 on an outer circumferential surface 66 of first end 44 of motor shaft 28. The inside diameter of handle housing 4 is slightly smaller than the diameter measured from overhang to overhang on diametrically opposed flexible fingers 60. Thus when motor shaft 28 is inserted into handle housing 4, flexible fingers 60 are flexed inwardly to allow a portion of motor shaft 28 to pass into recess 22 in handle housing 4.

In one embodiment, the inner diameter of handle housing 4 abruptly increases to form a shoulder 68. When each of the overhangs 62 on the respective fingers 60 passes shoulder 68, the fingers 60 flex outwardly to their natural positions. If motor shaft 28 is moved in a direction to try to extract it from handle housing 4, overhang 62 on each of the flexible fingers 60 engages shoulder 68 and thus retains motor shaft 28 in handle housing 4. Overhang 62 is however not large enough to withstand any substantial force, and if a sufficient extraction force is applied to motor shaft 28, the motor shaft can be withdrawn from handle housing 4 since the extraction force could overcome the contact between overhang 62 of shoulder 68 and thus force flexible fingers 60 to flex inwardly and allow motor shaft 28 to be extracted. Nonetheless, overhang 62 and shoulder 68 do engage sufficiently to keep and retain motor shaft 28 in handle housing 4 under normal use conditions. In one embodiment, overhang 62 on each flexible finger 60 acts as a side wall for the O-ring groove 52 formed at first end 44 of motor shaft 28.

Generally, with respect to the positioning of vibratory means 24 in toothbrush 2, in one embodiment vibratory means 24 is positioned close to brush head 14, and possibly even in brush head 14, to maximize the effect of the vibratory means's vibrating motion. As shown in FIG. 3, when the brush shaft 12 is positioned about motor shaft 28, the vibrating vibratory means 24 is positioned within brush shaft 12 adjacent brush head 14. In one example, vibratory means 24 is positioned adjacent brush head 14, and not in brush head 14, so that there is sufficient room in brush head 14 to position bristle tufts 16, as well as needing to have a slim shaped brush head 14 for accessibility in one's mouth. However, as smaller vibratory means become available, its contemplated that vibratory means 24 could be positioned inside brush head 14 to efficiently drive brush head 14 as described herein. For example, a piezo-electric type of vibration motor may be positioned in brush head 14.

In one embodiment, vibratory means 24 includes an eccentric motor which rotates an off center weight 25 attached thereto. One motor which may be used for creating the vibration is a Jinglong Co. model OTL-6CL or equivalent. The OTL-6CL model is generally a 1.3V DC motor. However, any motor suitable for creating vibration that has a small enough size and can be powered by a battery the size of an AA battery or the like could be used. Off-center weight motor 24 provides a magnitude of tip motion (approximately 0.02 inches in the x and y directions) for brushing purposes, in one example.

In one embodiment, the vibrations generated by the vibratory means selected may cause the brush head to vibrate in a substantially orbital motion. However, in other embodiments, the vibrations generated by the vibratory means selected may cause the brush head to vibrate in any type of motion suitable for cleaning teeth including axial, horizontal, vertical, diagonal, and circular motions.

As illustrated in FIG. 4, in one embodiment, the isolation joint structure 18 is formed at the connection point of the motor shaft end and the top open end of the handle. The bottom end 44 of the motor shaft 28 is received within the top open end 26 of the handle 4 to form the isolation joint structure 18, in one embodiment. The isolation joint structure 18 illustrated in FIG. 13 includes a pair of O-rings 50 positioned at end 44 of motor shaft 28 and received inside open top end 26 of handle 4. O-rings 50 are resilient and flexible, and thus allow motor shaft 28 (and thus brush shaft 12) to move under the influence of vibratory means in a relatively isolated manner, such motion being relatively independent of handle 4. The amount brush shaft 12 moves separately from handle 4 depends on the resiliency and dampening characteristics of isolation joint structure 18. In one embodiment of the present invention, isolation joint structure 18 includes an O-ring 50 positioned within annular grove 52 of motor shaft 28, a second O-ring 50 positioned within a second annular groove 52 spaced away from the first O-ring 50. The O-ring annular grooves 52 are formed in the wall 54 of handle housing 4 to respectively receive the O-rings 50 on end 44 of motor shaft 28. The end 44 of motor shaft 28 having the O-rings 50 is inserted into handle housing 4, and the O-rings 50 are located in their respective grooves 52.

In FIG. 13, first end 44 of motor shaft 28 is shown received in top end 26 of handle housing 4. Again, isolation joint structure 18 is formed by the engagement of the O-rings 50 positioned on first end 44 of motor shaft 28 in the O-ring channels 52 formed in inner wall 54 of handle housing 4. In one embodiment, motor shaft 28 does not physically contact directly handle housing 4, and is spaced away from handle housing 4 by the O-rings 50. The isolation joint structurally isolates the brush shaft and motor shaft from the handle, meaning that there is no direct connection between the handle and those parts meant to vibrate. If the O-rings 50 are flexible and resilient, motor shaft 28 can move to some extent both in a vibrating manner (radially, circularly, or any other type of movement caused by drive motor 24), and/or in somewhat of an axial manner with respect to handle 4.

The purpose of isolation joint structure 18 is to reduce, modify, minimize, or attenuate the amount of vibration felt in handle 4 when motor 24 is vibrating in brush shaft 12 (or elsewhere) and causing bristles 16 to move. Isolation joint 18 between motor shaft 28 and handle 4 can include several different vibration dampening and elimination structures. Any type of isolation joint 18 that accomplishes this is contemplated by this invention, and could include a single or multiple cylindrical bushings 70 spacing brush shaft 12 from handle housing 4, such as that shown in FIGS. 14 and 15.

Figure 14:
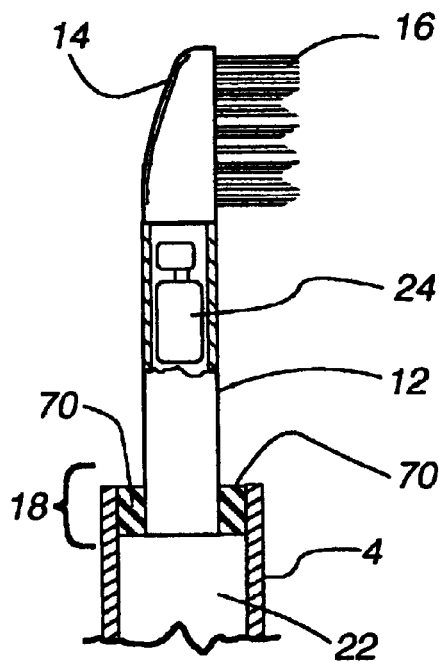
FIG. 14 is a side section view of a toothbrush, in accordance with one embodiment of the present invention.

In FIG. 14, brush shaft 12 is inserted in and retained in recess 22 of housing 4 by bushing 70 to form an isolation joint 18. It is contemplated that the bushing will be constructed of a vibration dampening material to absorb the vibration from the vibration means 24 contained in the brush head 14 or brush shaft 12. The embodiment of FIG. 14 will allow the brush shaft 12 and brush head 14 to vibrate relatively independently of the handle.

Figure 15:
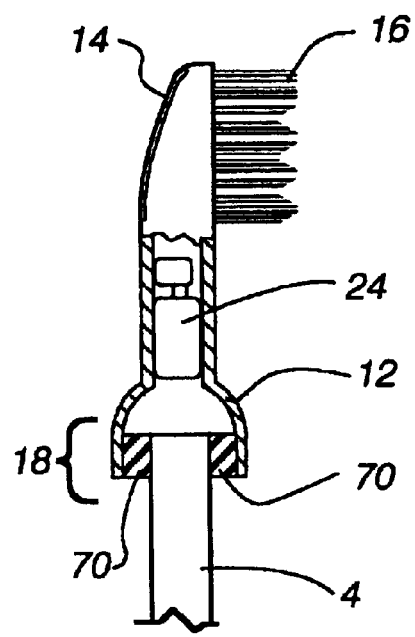
FIG. 15 is a side section view of a toothbrush, in accordance with one embodiment of the present invention.

In another embodiment in FIG. 15, handle 4 is inserted in and retained within brush shaft 12 by bushing 70 to form an isolation joint 18. Similar to the embodiment illustrated in FIG. 14, the bushing 70 is included to absorb the vibration from the vibration means 24 contained in the brush head 14 or brush shaft 12. Also, the vibration dampening bushing 70 will allow the brush shaft 12 and brush head 14 to vibrate relatively independently of the handle 4. Although the circumference of the handle illustrated in FIG. 15 is substantially smaller than that of the brush shaft, it is contemplated that the circumference of the handle 4 will expand along the length of the handle away from the bushing 70.

Figure 16:
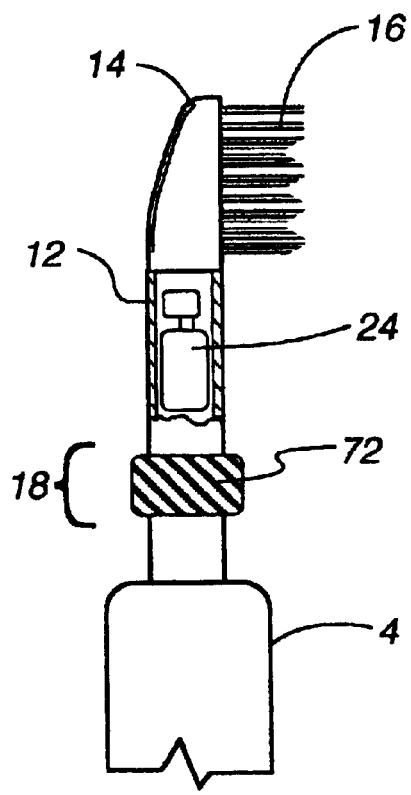
FIG. 16 is a side section view of a toothbrush, in accordance with one embodiment of the present invention.

In another embodiment illustrated in FIG. 16, isolation joint 18 could be a flexible section 72 positioned in brush head 14 or handle 4 so long as the flexible section 72 is positioned between and structurally isolates motor 24 and handle 4. Flexible section 72 can be made out of rubber, elastomer, or any kind of vibration dampening material suitable for the purpose.

Figure 17:
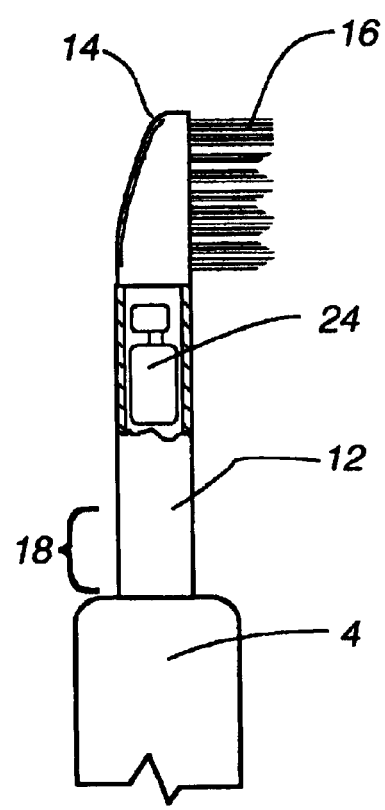
FIG. 17 is a side section view of a toothbrush, in accordance with one embodiment of the present invention.

Referring to another embodiment in FIG. 17, the entire brush shaft 12 (and motor shaft 28) could be made of a flexible material with motor 24 mounted therein, with a section of brush shaft 12 (including motor shaft 28) between motor 24 and handle 4 acting as the isolation joint 18. Flexible brush shaft 12 could be made of any type of elastomer or such material as would allow for flexible vibratory motion as a result of motor 24 (or other type of vibratory drive motor). The entire brush shaft 12 could be flexible or only sections thereof.

Figure 18:
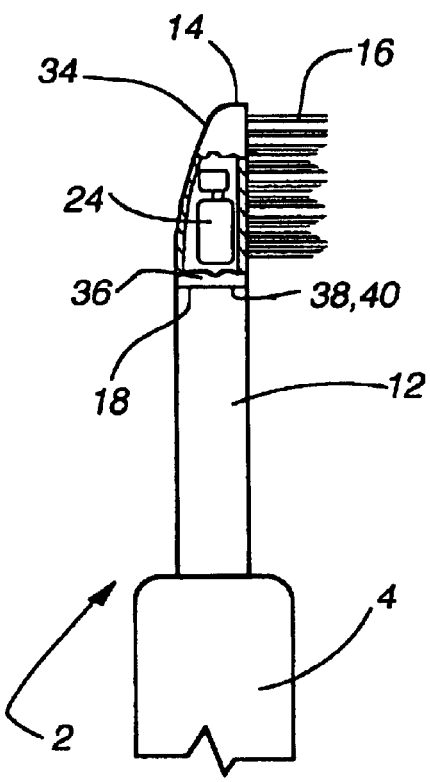
FIG. 18 is a side section view of a toothbrush, in accordance with one embodiment of the present invention.
Figure 19:
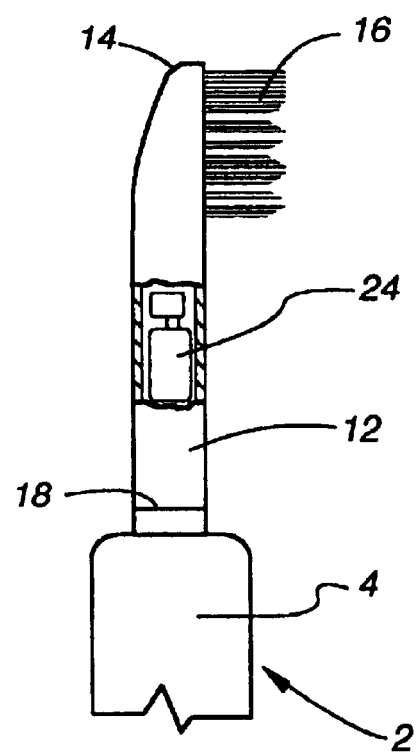
FIG. 19 is a side section view of a toothbrush, in accordance with one embodiment of the present invention.
Figure 20:
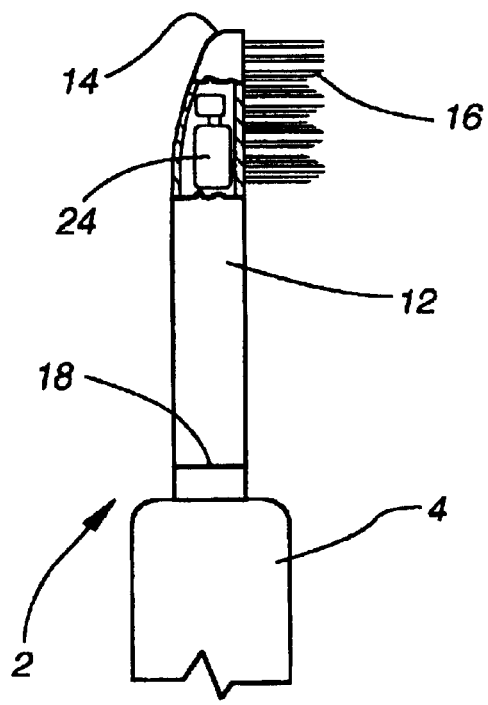
FIG. 20 is a side section view of a toothbrush, in accordance with one embodiment of the present invention.

FIGS. 18–20 show the vibratory means 24 and isolation joint 18 located on various portions of a toothbrush. In FIG. 18, the vibratory means 24 are located in brush head 14 and the isolation joint 18 is located at base 40 of brush head 14. The design in FIG. 18 reduces the vibrations of the vibratory means from transferring to the handle portion of the housing.

In FIG. 18, a brush head 14 may be attached to brush shaft 12 with a snug fit on the top of shaft 12 and into the top 34 of recess 36 of brush head 14. A circumferential snap attachment feature 38 circumferentially locates and axially retains the bottom 40 of brush head 14 to shaft 12.

In FIG. 19, the vibratory means 24 are located in brush shaft 12 and the isolation joint 18 is located in brush shaft 12. The location of the vibratory means 24 in the embodiment illustrated in FIG. 19 would affect the amount of vibrations translated to both the handle and the bristles. The amount of vibration to the bristles would likely be less than that in the FIG. 18 embodiment and the amount of vibration translated to the handle may be slightly more than that in the FIG. 18 embodiment.

In FIG. 20, the vibratory means 24 are located in brush head 14 and the isolation joint 18 is located in brush shaft 12 towards handle 4. In this embodiment, the vibration will likely be maximized in the brush head and bristles. However, the vibration felt in the handle may be slightly greater than in the embodiment of FIG. 18.

In addition to the embodiments described above, additional embodiments including optional features are contemplated. Examples of such features are discussed in greater detail below.

As particularly illustrated in FIG. 3, the connection leads 23a,b are connected from motor 24 to battery 10 through isolation joint 18. In one embodiment, cylindrical bore 42 is formed through the center 76 of motor shaft 28 thus allowing the leads 74 to pass therethrough to motor 24. In any of the other embodiments described herein, the passage of the leads 74 therethrough would be equally simple.

In any of the above isolation joint structures 18, or any other contemplated by this invention, the portion of toothbrush 2 which includes motor 24 (i.e., motor shaft 28/brush shaft 12) can move with respect to the other portion of toothbrush 2 from which it is isolated. The movement of the motor-including portion can be in a twisting manner, a vibrating manner, an orbital manner, a rotational manner, or any other type of motion helpful for cleaning teeth.

In one embodiment, the vibratory means 24 is positioned as close to brush head 14 as possible. Such positioning helps, even without an isolation joint 18 between vibratory means 24 and handle 4, to more efficiently drive brush head 14 and only residually drive handle 4. In this example, isolation joint 18 increases the effectiveness of positioning vibratory means 24 near or in brush head 14. When the placement of vibratory means is as close to brush head 14 as possible, the location of isolation joint 18 need only be on the handle 4 side of the vibratory means placement. In other words, isolation joint 18 may be located between vibratory means and handle 4. Thus, isolation joint 18 could be closer to brush head 14 than to handle 4, in one embodiment.

The end cap may also include an on/off switch for actuating the device. FIGS. 21—23 show a combination switch and battery holder end cap 92 used in one embodiment. The end cap combination 92 provides a sealed assembly, and includes two electrically non-conductive parts 122 and 124. Part 124 may be secured into an interior portion of handle 132 at its end.

Electrically conductive parts 126 and top battery contact 130 are assembled into housing 124 which may be fixed in handle 132. Battery carrier 122 holds lower contact strip 128 axially, but not rotationally fixed, into housing 132. The limits of rotation of housing 132/battery carrier 122 assembly are fixed by a radially protruding rib 140 that is received by a corresponding groove in housing 132. Similarly an axially protruding bump 144 formed on a flexible portion of battery carrier 122 is received by either of two corresponding grooves in housing 132. Each of these grooves the rotational assembly (of 122 and 132) in one of two operating positions. Bump 144 and the flexible portion of the area surrounding bump 144 allows the assembly to "snap" from one operating position to the second operating position providing a positive tactile click as battery carrier 122 is rotated. When this occurs the top contact 126 is brought into physical and electrical contact with the bottom contact strip 128 which is in direct communication with a bottom (−) terminal of a battery. This action causes a complete electrical path from a top (+) terminal of a battery to top contact 130 through motor wires 74 back through contact strips 126, 128 causing motor 24 to operate.

A positive seal is achieved with O-ring 156 sealing between housing 132 and the inside diameter of housing 132 which provides a drip proof feature that prevents moisture from running down handle 132 and accumulating or running into the internal cavity of the device.

Figures 24, 25, 26:
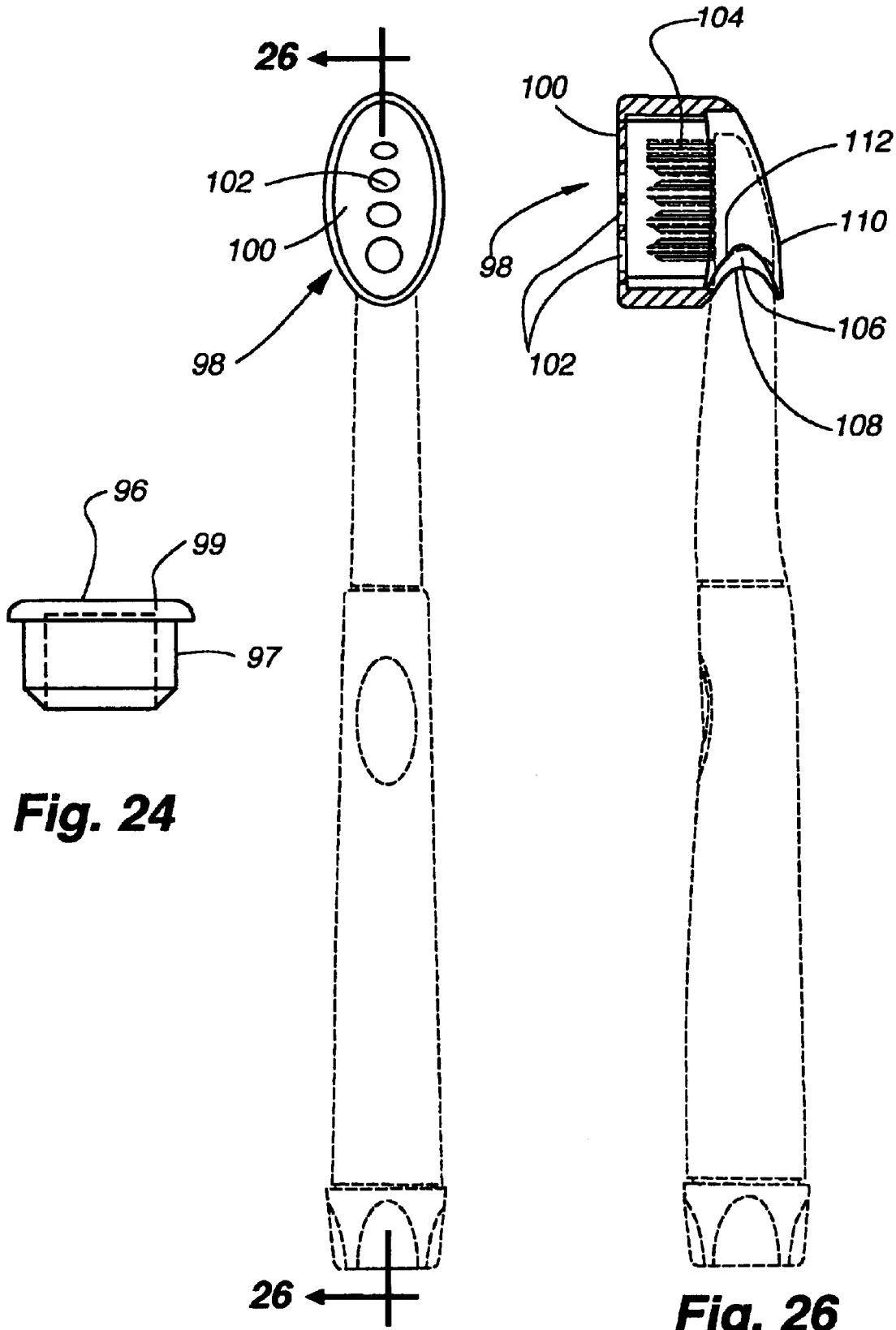
FIG. 24 is a side view of a motor shaft cap, in accordance with one embodiment of the present invention.
FIG. 25 is a front view of a brush head cover, in accordance with one embodiment of the present invention.
FIG. 26 is a side section view taken along line 26–26 in FIG. 25.

FIG. 24 shows an embodiment of a motor shaft cap 96, shown in FIGS. 4 and 12. Motor shaft cap 96 is a plug for the open top end 46 of motor shaft 28 to encase the motor within the cavity 48 of the motor shaft 28. In the embodiment illustrated in FIG. 24, cap 96 includes a plug portion 97 and an end cap 6 portion 99. Plug portion 97 extends into open end 46 of motor shaft 28. Portion 99 is of a larger diameter than plug portion 97, and cap 96 forms a fluid resistant seal to prevent fluids from entering into cavity 48.

FIGS. 25–26 show a brush head cover 98 that snaps onto and off of brush shaft 12 to cover brush head 14. A front face 100 of brush head cover 98 defines a plurality of holes 102 to allow air exposure and drainage of any moisture trapped on brush head 14 when brush head cover 98 is put on. Brush head cover 98 has a main body 104 that encloses bristles 16 when positioned on brush head 14 and has an attachment structure 106 which defines a partially cylindrical collar 108 attached to rear 110 of main body 104. This partially cylindrical collar 108 has sloped walls 112 to allow brush head 14 of toothbrush 2 to be initially placed into main body 104 and then collar 108 snapped around the perimeter of brush shaft 12 to secure cover 98 onto brush shaft 12 in a releasable manner. The sidewalls 114 of collar 98 are biased outwardly and around brush shaft 12 to provide a secure attachment.

Figure 27:
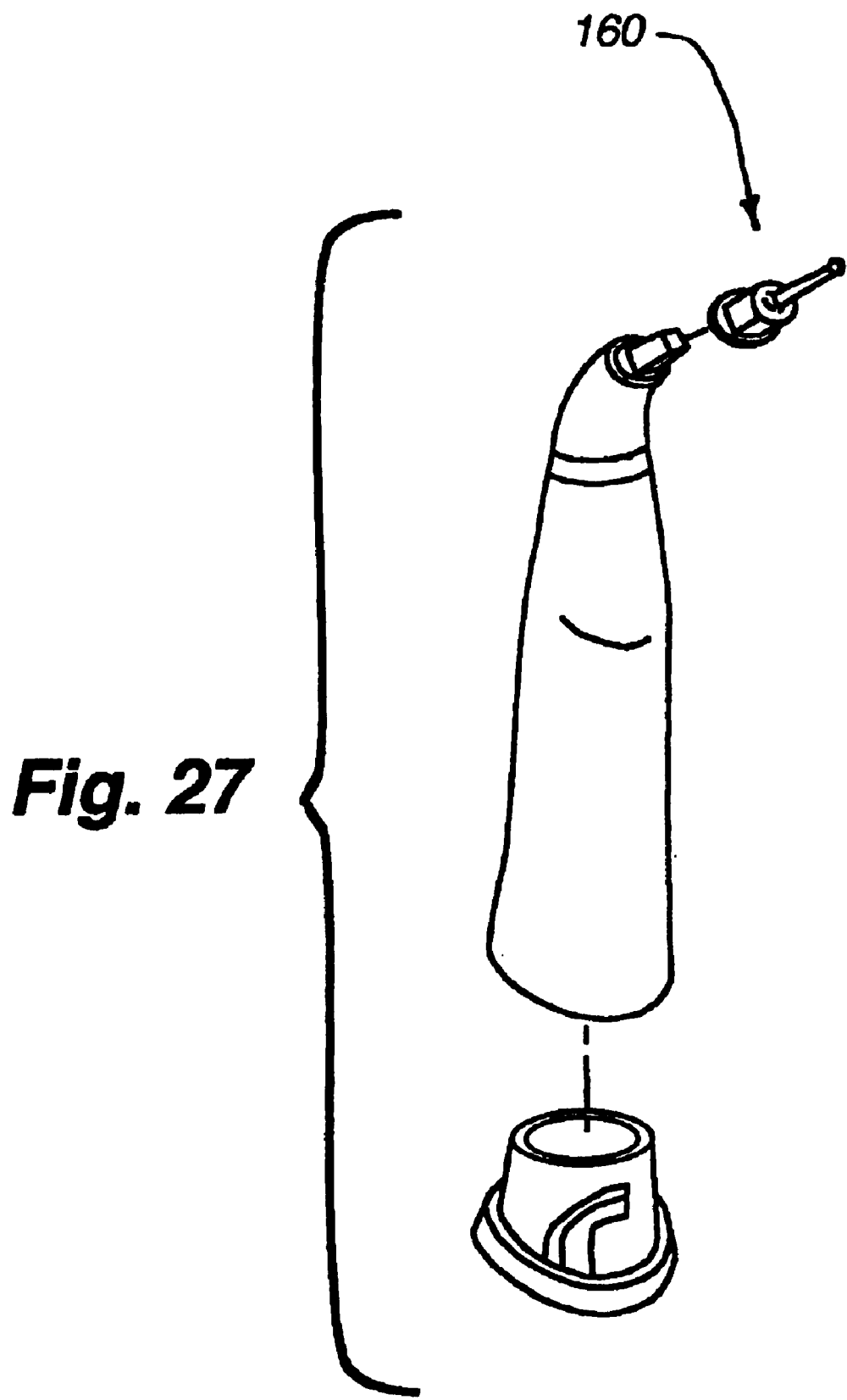
FIG. 27 illustrates a flossing tip and head which may be used with an embodiment of the present invention.

As shown in FIG. 27, at least one flossing element, as opposed to a set of bristles for use as a toothbrush, can be attached to the brush shaft or motor shaft for use in cleaning the interproximal spaces between a user's teeth.

All directional references used herein (e.g., upper, lower, upward, downward, left, right, leftward, rightward, top, bottom, above, below, vertical, horizontal, clockwise, and counterclockwise, etc.) are only used for identification purposes to aid the reader's understanding of the present invention, and do not create limitations, particularly as to the position, orientation, or use of the invention.

Although embodiments of the present invention have been described with a certain degree of particularity, it is understood that the present disclosure has been made by way of example, and changes in detail or structure may be made without departing from the spirit of the invention as defined in the appended claims.

What is claimed is:

1. A power toothbrush comprising:
   a handle;
   a brush head including bristles;
   a brush shaft connected with said brush head;
   a motor shaft connected with said handle and received in said brush shaft;
   a vibratory means positioned within said motor shaft for causing said bristles to vibrate; and
   a vibration isolation means for reducing vibrations from said vibratory means to said handle.

2. The power toothbrush of claim 1, wherein said vibration isolation means is positioned between said vibratory means and said handle.

3. The power toothbrush of claim 1, wherein said vibration isolation means includes a vibration dampening material positioned between said brush head and said handle to at least partially absorb vibrations caused by said vibratory means.

4. The power toothbrush of claim 1, wherein said vibratory means includes an eccentric motor.

5. The power toothbrush of claim 1, wherein said vibratory means is positioned near said brush head.

6. The power toothbrush of claim 1, wherein said vibration isolation means is positioned between said brush head and said handle.

7. The power toothbrush of claim 1, wherein said brush shaft and said brush head are integrally formed.

8. The power toothbrush of claim 1, wherein said vibratory means is positioned in said brush shaft.

9. The power toothbrush of claim 1, wherein said vibration isolation means is positioned between said brush shaft and said handle.

10. A power toothbrush comprising:
    a handle;
    a brush shaft;
    a brush head including bristles, said brush head adapted to be connected with said brush shaft;
    a motor shaft connected with said handle and received in said brush shaft;
    a vibratory means positioned in said motor shaft for causing said brush head and said bristles to vibrate; and
    a vibration isolation means positioned between said vibratory means and said handle for reducing the transfer of vibrations from said vibratory means to said handle.

11. The power toothbrush of claim 10, wherein said vibratory means includes an eccentric motor.

12. The power toothbrush of claim 10, wherein said vibratory means is positioned near said brush head.

13. The power toothbrush of claim 10, wherein said brush head and said brush shaft are integrally formed and are adapted to be connected with said handle.

14. The power toothbrush of claim 10, wherein said vibratory means is positioned in said brush shaft.

15. The power toothbrush of claim 10, wherein said vibration isolation means includes a vibration dampening material.

16. A power toothbrush comprising:
    a handle;
    a brush shaft;
    a brush head with bristles connected with said brush shaft; and
    an eccentric motor for causing the bristles to vibrate, wherein the eccentric motor is positioned entirely in said brush shaft distal from said handle and oriented parallel to a longitudinal axis of the power toothbrush;
    a vibration isolation means interposed between said brush shaft and said handle for reducing the transfer of vibrations from the brush shaft to the handle; and
    an annular spacing defined between said brush shaft and said handle.

17. The power toothbrush of claim 16, wherein said vibration isolation means is positioned between the brush head and the handle.

18. The power toothbrush of claim 16, wherein said vibration isolation means is positioned between the brush shaft and the handle.

19. The power toothbrush of claim 16, wherein said vibration isolation means includes a vibration dampening material.

20. The power toothbrush of claim 16, wherein said annular spacing permits said brush shaft to move with respect to said handle in a vibratory manner.

21. A power toothbrush comprising:

a handle;

a brush head including bristles, said brush head connected with said handle;

a rotary vibratory motor for causing said bristles to vibrate, said rotary vibratory motor positioned entirely in said brush head distal from said handle and oriented parallel to a longitudinal axis of said power toothbrush; and a vibration isolation means for reducing the transfer of vibrations from said rotary vibratory motor to said handle.

22. A toothbrush, comprising:

a handle having a first open end;

a brush shaft having a first end for receipt in said first open end of said handle, and a second end having at least one bristle element extending therefrom;

a vibration means positioned in said brush shaft adjacent to said at least one bristle element; and a vibration damping structure positioned between said first open end of said handle and said first open end of said brush shaft when received in said first open end of said handle, said vibration damping structure comprising:

a first O-ring positioned around said first end of said brush shaft;

a second O-ring positioned around said first end of said brush shaft and spaced away from said first O-ring;

said O-rings forming the sole structural connection between said brush shaft and said handle;

wherein said vibration damping structure reduces the vibrations caused by said vibration means passing to said handle from said brush shaft.

* * * * *

UNITED STATES PATENT AND TRADEMARK OFFICE
CERTIFICATE OF CORRECTION

PATENT NO. : 6,920,659 B2
DATED : July 26, 2005
INVENTOR(S) : Joe W. Cacka and Howell H. Chiles It is certified that error appears in the above-identified patent and that said Letters Patent is hereby corrected as shown below:

<u>Title page,</u>
Item [60], Related U.S. Application Data, delete "60/261,575" and replace with -- 60/261,515 --.

Signed and Sealed this

Fourth Day of October, 2005

JON W. DUDAS
*Director of the United States Patent and Trademark Office*